(12) United States Patent
Masotti et al.

(10) Patent No.: US 12,078,852 B2
(45) Date of Patent: Sep. 3, 2024

(54) OPTICAL FIBER DEVICE FOR LASER THERMAL ABLATION AND THERMAL THERAPY

(71) Applicant: ELESTA S.P.A., Calenzano (IT)

(72) Inventors: Leonardo Masotti, Sesto Fiorentino (IT); Luca Breschi, Vaiano (IT)

(73) Assignee: ELESTA S.P.A., Calenzano (IT)

( * ) Notice: Subject to any disclaimer, the term of this patent is extended or adjusted under 35 U.S.C. 154(b) by 839 days.

(21) Appl. No.: 15/734,833

(22) PCT Filed: Jun. 4, 2019

(86) PCT No.: PCT/IB2019/054631
§ 371 (c)(1),
(2) Date: Dec. 3, 2020

(87) PCT Pub. No.: WO2019/234623
PCT Pub. Date: Dec. 12, 2019

(65) Prior Publication Data
US 2021/0231886 A1 Jul. 29, 2021

(30) Foreign Application Priority Data
Jun. 5, 2018 (IT) .................. 102018000006054

(51) Int. Cl.
*G02B 6/42* (2006.01)
*A61B 18/22* (2006.01)
(Continued)

(52) U.S. Cl.
CPC ............ *G02B 6/4206* (2013.01); *A61B 18/22* (2013.01); *A61B 2018/00577* (2013.01);
(Continued)

(58) Field of Classification Search
CPC .... G02B 6/4206; G02B 6/4296; A61B 18/22; A61B 2018/00577; A61B 2018/2266; A61N 5/0625; A61N 5/067
See application file for complete search history.

(56) References Cited

U.S. PATENT DOCUMENTS

| | | | |
|---|---|---|---|
| 5,119,458 A * | 6/1992 | Okamoto | B24B 19/165 |
| | | | 359/332 |
| 5,782,822 A | 7/1998 | Telfair et al. | |

(Continued)

FOREIGN PATENT DOCUMENTS

| | | |
|---|---|---|
| CN | 101144876 A | 3/2008 |
| CN | 101919733 A | 12/2010 |

(Continued)

*Primary Examiner* — Michael P Mooney
(74) *Attorney, Agent, or Firm* — McGlew and Tuttle, P.C.

(57) ABSTRACT

The device comprises at least a laser source (5); an optical fiber (1) with an optical radiation entrance end (1.2) and an optical radiation output end (1.1); and a coupling system (8) for coupling the laser source (5) and the optical fiber (1), adapted to inject an optical radiation emitted by the laser source (5) into the entrance end (1.2) of the optical fiber (1). The optical fiber (1) is a multi-mode optical fiber. The coupling system (8) is adapted to inject the optical radiation into the optical fiber (1) with such an inclination (a) as to reduce or eliminate the fundamental transmission mode and to promote the transmission according to at least one higher-order transmission mode The optical radiation at the output end (1.1) of the optical fiber (1) has a cone-shaped distribution (3) wherein the intensity is maximal on the peripheral volume of an emission cone and is minimal inside the emission cone.

25 Claims, 16 Drawing Sheets

(51) Int. Cl.
*A61B 18/00* (2006.01)
*A61N 5/06* (2006.01)
*A61N 5/067* (2006.01)

(52) U.S. Cl.
CPC ..... *A61B 2018/2266* (2013.01); *A61N 5/0625* (2013.01); *A61N 5/067* (2021.08)

(56) References Cited

U.S. PATENT DOCUMENTS

| | | | |
|---|---|---|---|
| 5,908,416 | A | 6/1999 | Costello et al. |
| 8,582,613 | B1 | 11/2013 | Kim et al. |
| 8,740,957 | B2 | 6/2014 | Masotti |
| 2004/0102764 | A1 | 5/2004 | Balling |
| 2006/0217693 | A1 | 9/2006 | Gowda et al. |
| 2006/0219673 | A1 | 10/2006 | Varnham et al. |
| 2006/0253178 | A1 | 11/2006 | Masotti |

FOREIGN PATENT DOCUMENTS

| | | | | |
|---|---|---|---|---|
| CN | 101930096 | A | 12/2010 | |
| CN | 103269653 | A | 8/2013 | |
| DE | 0362466 | A2 * | 4/1990 | ........... G02B 6/4296 |
| EP | 0362466 | A2 | 4/1990 | |
| EP | 0366856 | A2 | 5/1990 | |
| EP | 0402017 | A2 | 12/1990 | |
| WO | 9314430 | A1 | 7/1993 | |
| WO | 2018087012 | A1 | 5/2018 | |
| WO | 2018087013 | A1 | 5/2018 | |
| WO | 2018087014 | A1 | 5/2018 | |
| WO | 2018087015 | A1 | 5/2018 | |

* cited by examiner

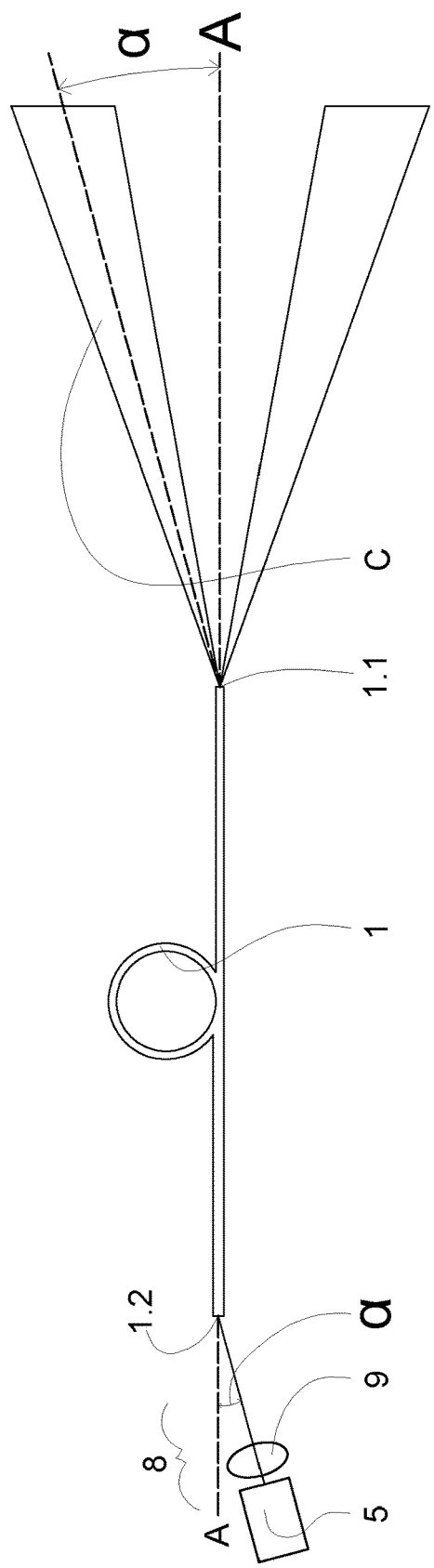

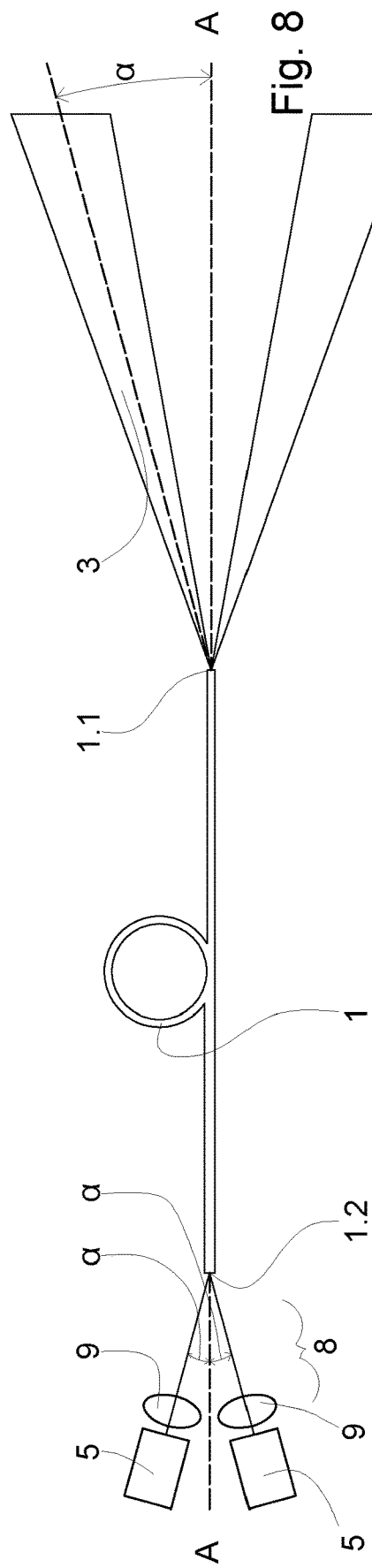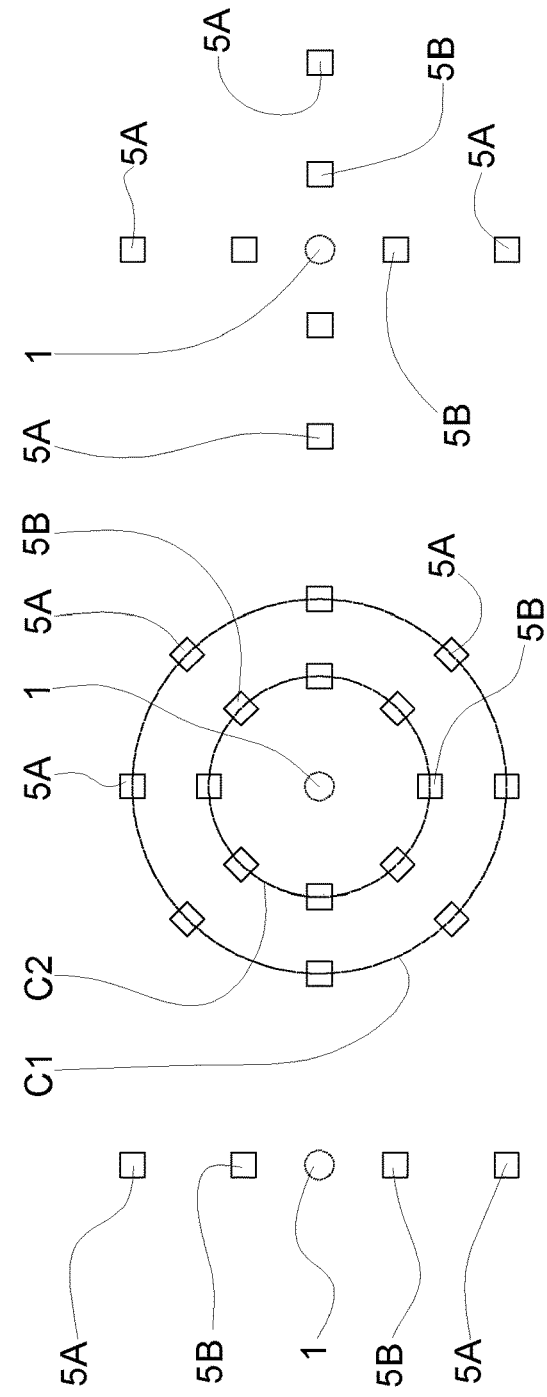

OPTICAL FIBER DEVICE FOR LASER THERMAL ABLATION AND THERMAL THERAPY

TECHNICAL FIELD

The present invention relates to the use of an optical fiber-guided laser radiation for medical and surgical applications. Embodiments disclosed herein relate to thermal therapy and laser thermal ablation treatments, as well as to treatments where the energy generated by a laser source is conveyed via optical fiber towards an in-vivo tissue volume to be treated.

PRIOR ART

In the field of laser thermal ablation, the optical fiber-guided light, inserted percutaneously or intra-surgically through needles acting as introducers within the area to be treated, is absorbed by the tissues and converted into heat. The local temperature rise causes a series of biological phenomena, including cell death causing coagulative necrosis of tissues. This principle has been used for years for treatments in surgical and specifically oncological field in order to achieve complete necrosis, or cyto-reduction (laser induced cyto-reduction) in several organs (liver, prostate, thyroid, kidney, pancreas, breast, lung, etc.) affected by different pathologies.

A problem in these applications is to have spherical thermal lesions, either high-sphericity lesions or medium-ellipticity lesions. Round or approximately round treatment volumes better adapt to the tumor shape, which is usually round.

Currently, for laser thermal ablation flat-tip quartz optical fibers are used, characterized by being front-emitting. This kind of emission causes ellipsoid-like shaped thermal lesions with sphericity ratio of about 0.6-0.7; wherein by sphericity ratio is understood as the ratio between the minor axis and the major axis of the ellipse constituted by the longitudinal section of the lesion, i.e. the section according to a plane containing the optical axis of the fiber. The major axis is in line with the fiber direction, i.e. with the fiber axis.

In organs of small dimension or for subcapsular or exophytic lesions, the non-round shape of the lesion can make it impossible for the patient to be treated if the only available access (in terms of orientation of the fiber introducer and presence of vital structures that cannot be crossed) causes a thermal treatment outside the involved organ, i.e. transferring heat to, for example, vital structures outside the organ, such as vessels, ducts, nerves, other organs such as the heart, intestine etc. In these cases, even if, after having assessed the risk-benefit ratio, the decision is taken to carry out the treatment, serious complications can occur in the acute phase of post-treatment, as well as long-lasting or even permanent and disabling effects.

In order to better illustrate the difficulties due to the shape of the ablation volume using normal flat-tip optical fibers, reference should be made to FIG. 1. The figure schematically shows a cross section of a thyroid T with a thyroid cancer CT to be ablated. TR indicates the trachea, E the esophagus, G the jugular vein, C the carotid artery, and FN1, FN2 indicate two nerve bundles. In particular, FN2 indicates the recurrent laryngeal nerve.

The cancer CT cannot be treated with the laser ablation technique of the prior art using flat-tip optical fibers, due to the cancer in subcapsular position, i.e. close to the edge of the organ. Furthermore, the cancer CT is near a fundamental nerve structure FN2, controlling the vocal cords, and near the esophagus E and the trachea T. Accessing with an introducer from left to right (path F1) is impossible due to the shape of the thermal lesion LT1 which would be obtained through laser radiation emitted by the flat-tip optical fiber. In fact, to have a dimension of the thermal lesion LT1 sufficient to ensure the complete ablation of the tumor mass, the lesion, due to its ellipsoid-like shape, would protrude from the organ T. This would cause damages to the recurrent laryngeal nerve with temporary or permanent paralysis of the vocal cord, leading to changes in the voice. Accessing with an introducer from right to left according to the path F2 would be optimal to ensure correct and safe ablation of the cancer CT, but it is impossible due to the presence of an anatomical structure (trachea TR) that cannot be crossed by the introducer and the fiber.

Summarizing, vital anatomical structures can prevent proper access to the lesion to be removed and at the same time can prevent complete ablation without risks of irreversible damages. The example case in question, illustrated in FIG. 1, would have been solved with a device capable of producing a round shaped ablation with access from left to right (path F1).

Optical fibers have been provided with output ends suitably shaped to have a round or nearly round emission. For example, fibers have been provided with conical, frusto-conical, pyramidal, frusto-pyramidal, or round tip. Diffusers have been also provided on the fiber tip, suitably shaped to have a round or nearly round emission. These attempts were unsuccessful. In fact, during the laser thermal ablation, the temperature in the area surrounding the fiber tip can reach 300-400° C., in the tip area where the high power densities allow the evaporation of intra and endocellular water and the subsequent removal of dehydrated tissue. If the fiber tip has a conical or round shape, an isotropic emission is obtained, i.e. the radiation is emitted in all directions, including backwards, that is towards the fiber. The backward propagated radiation acts on the tissues in the proximal area of the fiber and causes the fiber to overheat. The temperatures at the output end of the fiber cause the destruction of the outer layer of the fiber (jacket and buffer), which is generally made of plastic. The outer layer is thus totally removed and the quartz fiber remains uncovered and devoid of the protective layer. It has been noted that the fiber damaged in this way is extremely fragile. It is so fragile that it cannot be used in the medical-surgical field, because there is the risk that it breaks during the treatment or in the extraction step, with consequent release of quartz fragments in the patient's body.

In order to solve this problem, protective cases or caps have been provided for the tip of the fiber, which are optically transparent and resistant to high temperatures. However, these devices are complex and expensive, which makes them unsuitable for single-use. Moreover, the protective case or cap increases the dimension of the device, therefore affecting the invasiveness of treatment.

In other applications, the laser radiation injected into the fiber is used for thermal treatments (laser thermal therapy), where side-emitting fiber is required, i.e. where the emission shall be transversal to the axis of the optical fiber. To this end, diffusers are provided applied to the output end of the optical fiber. Examples of devices for these applications are described in WO2018/087015; WO2018/087014; WO2018/087013; WO2018/087012.

A significant part of the power is emitted frontally, i.e. in the direction of the optical fiber axis. This can cause inconveniences, including thermal damage to the tissues of vital organs. In some known embodiments, this power is shielded and is therefore lost. In these applications it would be important to increase the ratio between laterally emitted power and total power conveyed by the fiber, i.e. it would be advisable to reduce as much as possible the amount of power conveyed by beams parallel to the fiber axis and emitted frontally.

There is therefore a need for providing a device, which allows to overcome, at least partially, the drawbacks of known devices. In particular, there is a need for providing devices for laser thermal ablation, which allow to have thermal lesions of suitable shape without the need for complex, expensive and invasive devices. There is also the need to optimize the lateral emission in devices provided with diffuser for laser thermal therapy.

SUMMARY

To overcome, at least partially, the drawbacks and limits of the prior art devices, a device is provided comprising: at least a laser source; an optical fiber with an optical radiation entrance end and an optical radiation output end; a coupling system for coupling the laser source and the optical fiber, adapted to inject an optical radiation emitted by the laser source into the entrance end of the optical fiber. The optical fiber is preferably a flat end optical fiber, i.e. where the optical fiber output end is flat, i.e. in which the output end of the optical fiber is flat, i.e. substantially plane and substantially orthogonal to the optical fiber output axis. The optical fiber is a multi-mode optical fiber. Furthermore, the coupling system is adapted to inject the optical radiation into the optical fiber with such an inclination as to reduce or eliminate the fundamental transmission mode and to promote the transmission according to at least one higher-order transmission mode, so that the optical radiation at the output end of the optical fiber has a cone-shaped distribution, wherein the intensity is maximal on the peripheral volume of an emission cone and is minimal inside the emission cone.

For greater efficiency, in advantageous embodiments the optical fiber is a tapered optical fiber, wherein the diameter of the output end is smaller than the diameter of the entrance end. Thanks to this shape, it is possible to have a particularly wide emission cone, wherein the cone width is larger than the inclination of the entering laser beam. The output energy is therefore better distributed, wherein the emission cone opening angle is larger than the acceptance angle of the optical fiber, the acceptance angle being a limit to the inclination range of the beam entering the fiber.

In advantageous embodiments, the maximal intensity of the optical radiation at the optical fiber output end, on the outer volume of the emission cone is at least twice, preferably at least three times, or even at least four or more times, the minimal intensity in the central volume of the emission cone.

The coupling system is adapted to inject an optical radiation beam into the optical fiber inclined, with respect to the axis of the optical fiber, by an angle different than zero. However, the inclination angle is smaller than the optical fiber acceptance angle. Injecting the optical radiation inclined leads to a substantial reduction or elimination of the fundamental transmission mode to the advantage of the higher-mode transmission modes, according to which the exiting optical radiation is distributed conically, the intensity thereof being minimal on the axis of the emission cone and maximal on the edge thereof.

Further features and embodiments of the device will be described below and defined in the attached claims, which form an integral part of the present description.

According to a further aspect, a method for emitting an optical radiation from a fiber is disclosed, comprising the steps of:
injecting an optical radiation into an optical fiber with an angle, with respect to an optical axis of the optical fiber, different than zero and smaller than an acceptance angle of the optical fiber, so as to propagate an optical radiation along said optical fiber mainly according to a higher-order transmission mode, eliminating or reducing the fundamental transmission mode;
emitting the optical radiation at an output end of the optical fiber according to an emission cone, wherein the intensity of the exiting optical radiation is maximal on an outer volume of the emission cone and is minimal in an inner volume of the emission cone.

BRIEF DESCRIPTION OF THE DRAWINGS

The invention will be better understood by following the description and the accompanying drawing, which shows a non-limiting example of embodiment of the invention. More in particular, in the drawing:

FIG. 7 is a diagram of a coupling system for coupling a laser source and an optical fiber in a further embodiment;

FIG. 8 shows a diagram of a system comprising a pair of diode laser sources and focusing lenses for injection into the optical fiber;

FIGS. 8A, 8B, and 8C are diagrams illustrating possible arrangements of multiple laser sources for the device of FIG. 8;

DETAILED DESCRIPTION

Figure 1:
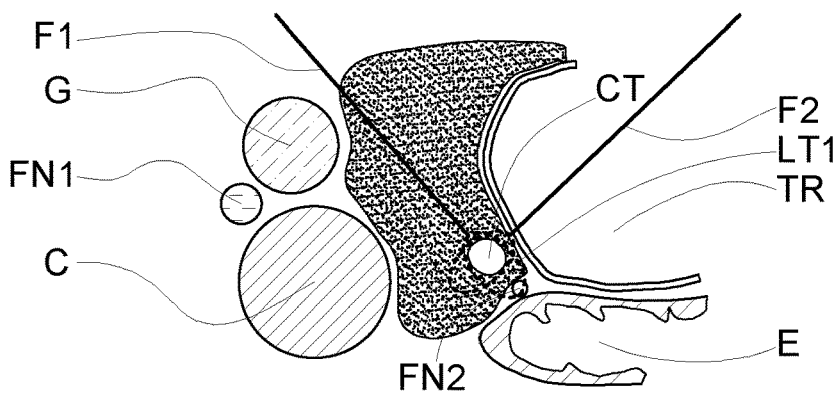
FIG. 1, already described, is a schematic cross-section of a thyroid with a thyroid carcinoma to be removed.

In order that the intensity of the optical radiation exiting from the fiber is optimally distributed, the energy amount, and therefore the power, transmitted along the optical fiber according to the fundamental mode should be reduced or eliminated, and the amount of energy transmitted along the optical fiber according to higher-order modes should be increased. To this end, the optical radiation is injected according to rays inclined with respect to the fiber axis, essentially avoiding injecting into the fiber rays that can propagate without reflection, according to the fundamental mode. The radiation exiting from the fiber is distributed according to a cone, the half-opening whereof corresponds to the angle of injection of the radiation into the fiber. In this way, at the output end of the optical fiber, a concentration of emission of laser radiation is obtained on a conical hollow volume. In the area inside the laser radiation exit cone, in line with the exit cone, the radiation intensity is minimal, and can be approximately zero, or in any case insufficient for frontal thermal ablation, that is in line with the optical fiber.

It has been observed that with a radiation distribution of this type, nearly round thermal lesions can be obtained using flat-tip fibers, therefore without the need for complex mechanical processing of the fiber. Moreover, since the exiting optical radiation propagates forwards and not backwards, the coating is not damaged by overheating; the fiber remains intact and protected, without the need for additional protective cases or coatings.

For better understanding the following description, here below some principles on light radiation transmission through optical fiber will be mentioned.

It is known that, in order for a light ray incident on the entrance end of an optical fiber to propagate inside the fiber, it is necessary (although not sufficient) that the angle formed between the ray and the optical axis of the fiber is smaller than the opening angle of the fiber. This is because along the optical fiber the following rays can propagate: the rays that are not incident on the fiber/coating interface, i.e. the rays propagating parallel to the optical axis of the fiber, and the rays that, although incident on the interface, are reflected inside the fiber and not refracted towards the coating.

The acceptance angle $\alpha_a$ of the optical fiber is defined according to the refractive index $n_1$ of the material forming the fiber core and to the refractive index $n_2$ of the material forming the coating. This acceptance angle is defined by the following formula:

$$\sin \alpha_a = ((n_1^2 - n_2^2)/n)$$

where n is the refractive index of the propagation medium outside the fiber.

In case of air propagation it is possible to assume n=1, therefore $$\alpha = \arcsin(NA)$$

The numerical aperture of the fiber is defined as the value $$NA = (n_1^2 - n_2^2)$$

The light radiation that propagates inside the fiber is refracted in an exit cone having an apex angle $2\alpha_a$.

As it is well known, not all the injection angles result in a guided propagation; inside the fiber propagate only the rays entering the fiber according to an angle, with respect to the axis of the fiber, that is smaller than the acceptance angle $\alpha_a$ and corresponds to one of the so-called "congruence angles $\alpha_m$" defined by the following formula:

$$\alpha_m = \arcsin\left(\frac{\lambda}{2\pi d}(m\pi + \phi_m)\right)$$

where m is an integer, d is the diameter of the fiber, $\lambda$ is the wavelength of light radiation and $\phi_m$ is the phase difference between the incident ray and the ray reflected on the interface between the core and the coating of the fiber, i.e. the phase variation due to reflection. This is due to the fact that in the optical fiber only the rays are propagated, for which the constructive interference condition is respected.

The discretization of the values of the injection angles, i.e. of the angles at which the radiation incident on the end of the fiber can propagate inside the fiber up to the output end, leads to the formation of optical fiber transmission modes, that are different modes of distributing the light intensity around the axis of the core, identified by the index m.

In practice, according to the invention, light rays are injected into the optical fiber according to congruence angles different than zero, in order that the light radiation, and therefore the energy, is transmitted according to higher-order transmission modes. In this way, the energy distribution at the output end of the optical fiber is concentrated around a conical surface, the opening whereof is equal to twice the congruence angle according to which the radiation has been injected. The optical radiation intensity is minimal inside the cone, where it can even be, in some cases, approximately zero or such as not to induce thermal damage or overheating.

By avoiding to inject the radiation according to an angle equal to zero, the fundamental transmission mode is essentially eliminated; therefore, at the output end there will be a very low light intensity in a direction parallel to the direction of the axis of the optical fiber, i.e. in a direction orthogonal to the exit side of the optical fiber It has been found that a hollow conical distribution of the intensity of the radiation emitted by the fiber allows to produce almost spherical thermal lesions, or in any case with a much higher sphericity ratio than the one which can be obtained with flat-tipped fibers and transmission mainly according to the fundamental mode. For example, thermal lesions can be obtained with sphericity ratio equal to or greater than 0.8, in some cases equal to, or greater than, 0.9.

Moreover, the emission according to a hollow cone ensures great advantages when using diffusers in laser thermal therapy treatments, as better explained below.

To take advantage of the propagation of optical radiation in higher modes by suppressing the fundamental mode, it is necessary to use multimode fibers. Moreover, in order to have a wide opening for the energy exiting the fiber, as this angle is equal to the entrance angle, it is advisable to use fibers with a large opening angle, i.e. with a high numerical aperture NA.

Currently, multi-mode fibers are available with a numerical aperture of 0.22; 0.37; 0.48 and 0.57, corresponding to acceptance angles of approximately 13°, 22°, 28° and 35°.

For a better understanding of the operation of a device according to the invention, compared to a conventional device, reference shall be made to FIGS. 2A-3E.

Figure 2A:
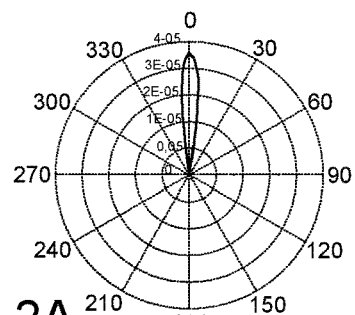
FIGS. 2A, 2B, 2C and 2D are emission diagrams of a flat-end optical fiber, wherein the optical radiation is injected according to the prior art technique.

FIG. 2A shows a polar chart, obtained for example with an optical radiogoniometer, using a flat-tip optical fiber with numerical aperture 0.22 and injecting the optical radiation according to the prior art, i.e. with the beam coaxial with the optical fiber. The chart has been obtained with a 652 nm laser diode. The optical radiation emitted by the optical fiber is strongly directional, i.e. focused on the fiber axis. The chart of FIG. 2B shows the emission profile of the same optical fiber, under the same conditions of use of FIG. 2A, in a Cartesian coordinate plane, wherein the emission angles are on the x-axis and the optical intensity in mW on the y-axis.

Figure 2B:
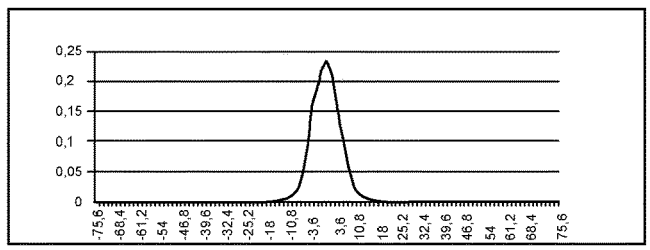
Figure 2C:
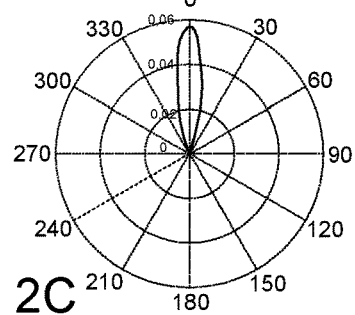
Figure 2D:
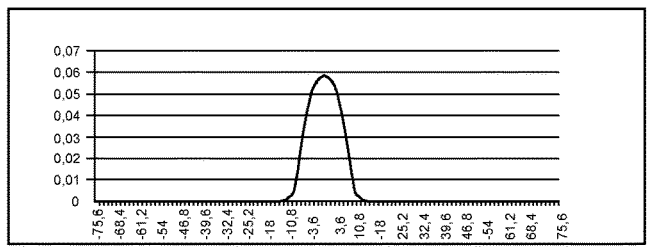

FIGS. 2C and 2D show the same charts of FIGS. 2A and 2B for an optical fiber with numerical aperture NA=0.37. In this case again, the emission of the optical radiation from the fiber is strongly directional, i.e. the power is emitted in a volume around the fiber axis.

Figure 3A:
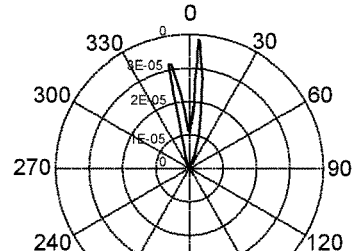
FIGS. 3A, 3B, 3C, and 3D are emission diagrams of a flat-end optical fiber wherein the optical radiation is injected according to what described herein.
Figure 3B:
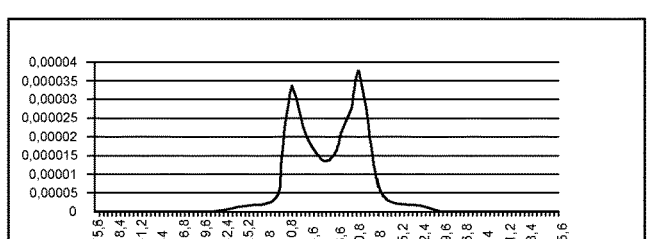

FIG. 3A shows a polar chart, obtained with an optical radiogoniometer, of the emission of a flat-tip optical fiber with numerical aperture NA=0.22, wherein the optical radiation, emitted by the same laser diode of FIGS. 2A-2D, has been injected inclined by an injection angle, or incidence angle, i.e. the angle with respect to the optical axis of the fiber, of 8°. FIG. 3B shows the same profile of emission intensity in a Cartesian plane, the angle being on the x-axis and the intensity on the y-axis.

Figure 3C:
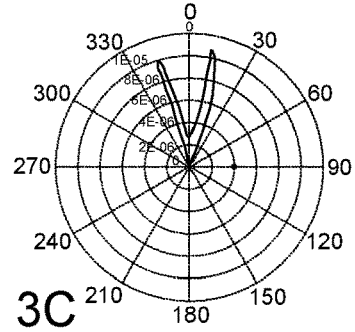
Figure 3D:
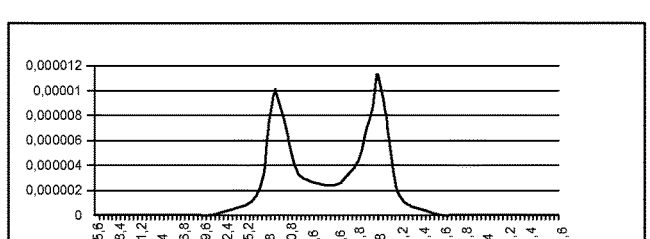

FIG. 3C shows a polar chart similar to that of FIG. 3A, for an optical fiber having a numerical aperture NA=0.37 and wherein the light radiation is injected into the fiber inclined by an entrance angle of 14°. FIG. 3D shows the same profile of the emission intensity of FIG. 3C, but in a Cartesian plane, with the angle on the x-axis and the intensity on the y-axis.

With reference to FIGS. 3A, 3B, the intensity of the exiting optical radiation is concentrated onto a cone with an opening of about 16° (that is, twice the entrance angle), with a negligible intensity in the center, i.e. in line (0° angle) with the optical fiber. In FIGS. 3C, 3D there is a similar distribution, but the cone has an opening of about 28°, twice the radiation injection angle (14°). In the diagrams of FIGS. 3A-3D the y-axis shows the optical intensity in Watts.

Figure 3E:
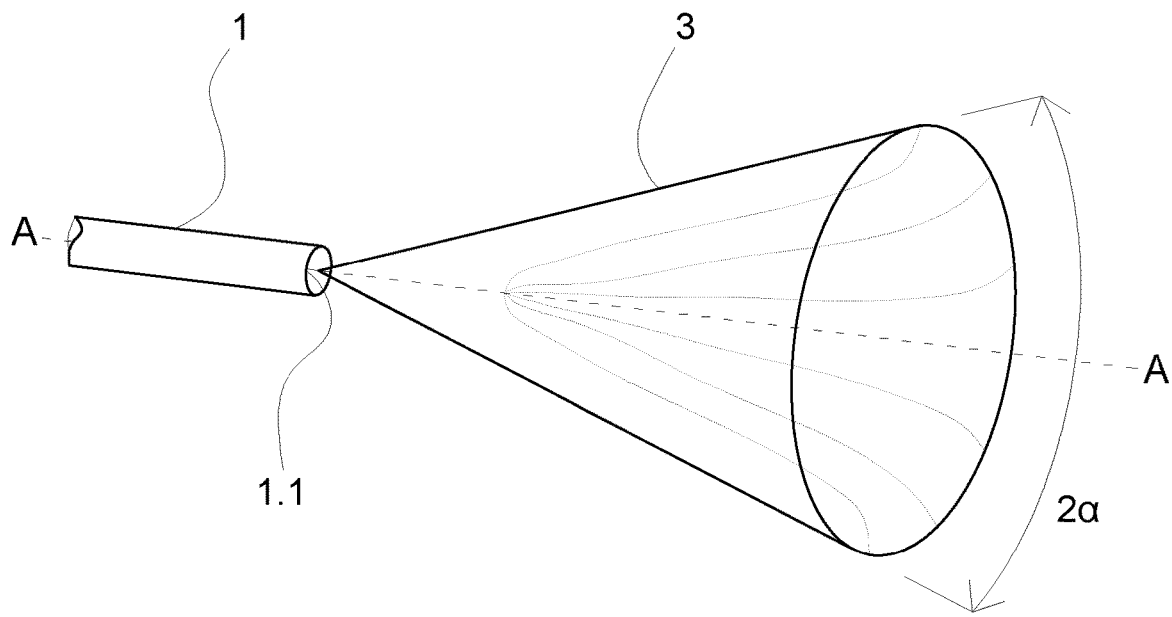
FIG. 3E is a schematic three-dimensional view of the energy distribution in the cone exiting from the optical fiber.

FIG. 3E schematically shows a qualitative three-dimensional representation of the intensity distribution of the light energy exiting from the optical fiber 1. Number 3 indicates the cone with opening 2α, wherein α is the injection angle (8° or 14° in the examples of FIGS. 2 and 3). Number 1.1 indicates the flat-tip output end of the optical fiber 1.

Figure 3F:
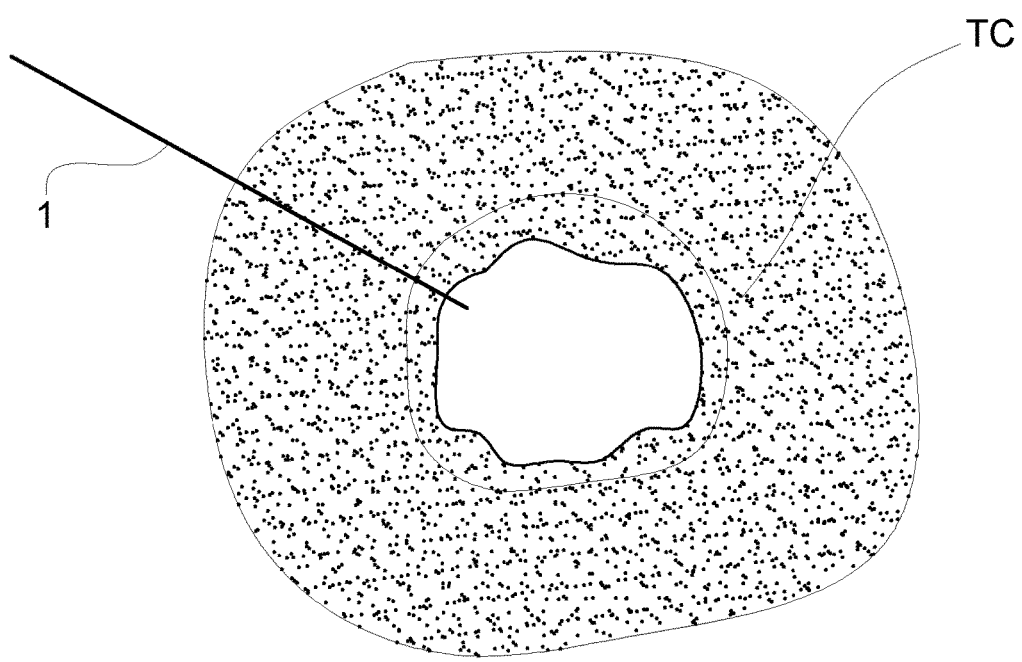
FIG. 3F shows a thermal lesion made with a device as described herein.

FIG. 3F shows the result obtained by treating an ex-vivo porcine liver with an optical fiber 1, in which the light radiation propagates according to modes other than the fundamental mode, resulting in a conical emission as illustrated in FIGS. 2, 3 and 3A. In FIG. 3F, number 1 indicates the optical fiber and CT indicates the tissue coagulation area, which is round or nearly round, i.e. with a sphericity ratio close to 1.

Now, with reference to FIGS. 4 to 8, various configurations will be described of the coupling system coupling the laser source and the optical fiber to inject the optical radiation into the optical fiber 1 and have a transmission according to one or more higher-order modes than the fundamental mode and, consequently, conical distribution of the exiting energy.

Figure 4:
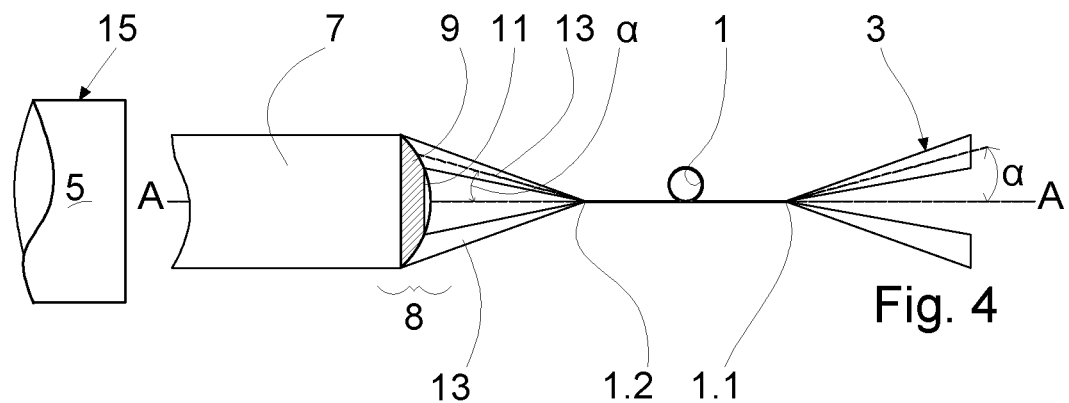
FIG. 4 is a diagram of a coupling system for coupling a laser source and an optical fiber in a first embodiment.

FIG. 4 schematically shows a laser source 5 emitting a beam 7, which is collected by a coupling system 8 to inject the radiation into the entrance end 1.2 of the optical fiber 1. In FIG. 4, number 1.1 indicates the output end or end of emission of the radiation from the optical fiber, and number 3 indicates the emission cone of the optical radiation from the optical fiber 1.

The coupling system may comprise a focusing lens 9, the focus of which is approximately on the entrance side of the optical fiber 1, at the entrance end 1.2. To eliminate the fundamental transmission mode, the focusing lens 9 is provided with a central shield 11, which is coaxial with the focusing lens 9 and reflects or absorbs the energy incident in the area surrounding the optical axis of the focusing lens 9. In this embodiment, the focusing lens 9 is coaxial with the optical fiber, i.e. the optical axis of the entrance end of the fiber coincides with the optical axis of the focusing lens 9. Thanks to the shield 11, only the radiation contained in a hollow cone 13 reaches the entrance side of the optical fiber 1. In this way, in the optical fiber 1 optical radiation is injected inclined by an angle α with respect to the optical axis A-A, and propagates according to a higher-order mode. At the exit of the optical fiber 1 there will be an emission cone 3 of opening 2α. The energy emitted in the inner volume of the emission cone 3 is nearly zero or in any case very low compared to the energy emitted in the surrounding conical hollow volume.

Figure 5:
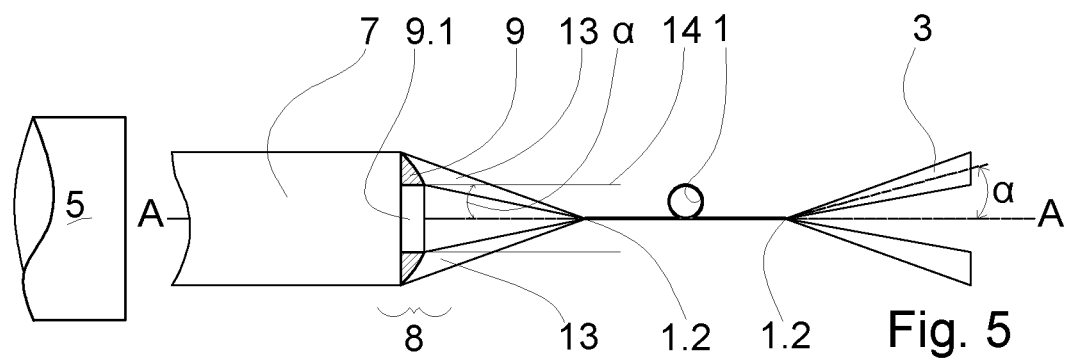
FIG. 5 is a diagram of a coupling system for coupling a laser source and an optical fiber in a further embodiment.

A similar effect can be obtained by using a focusing lens with a central hole, as shown in the embodiment of FIG. 5, where equal numbers indicate equal or equivalent parts to those of FIG. 4. Reference 9.1 indicates an axial hole passing through the lens 9. The portion of the beam 7 incident on the lens 9 which is in correspondence of the hole 9.1 is not focused and therefore a negligible part of the energy of this beam portion is injected into the fiber and propagates according to the fundamental mode. The annular portion of beam 7, incident on the lens 9 and focused by it at the entrance end 1.2 of the optical fiber 1, has an inclination α with respect to the optical axis A-A; therefore, the optical radiation exiting from the optical fiber 1 has a conical distribution 3.

For a better efficiency, avoiding to waste part of the light energy emitted by the laser source 5, in other embodiments the coupling system for coupling the laser source 5 and the optical fiber 1 may collect all the available optical radiation and injects it into the optical fiber 1 according to an axis inclined with respect to the optical axis of the fiber at the entrance end 1.2.

Figure 6:
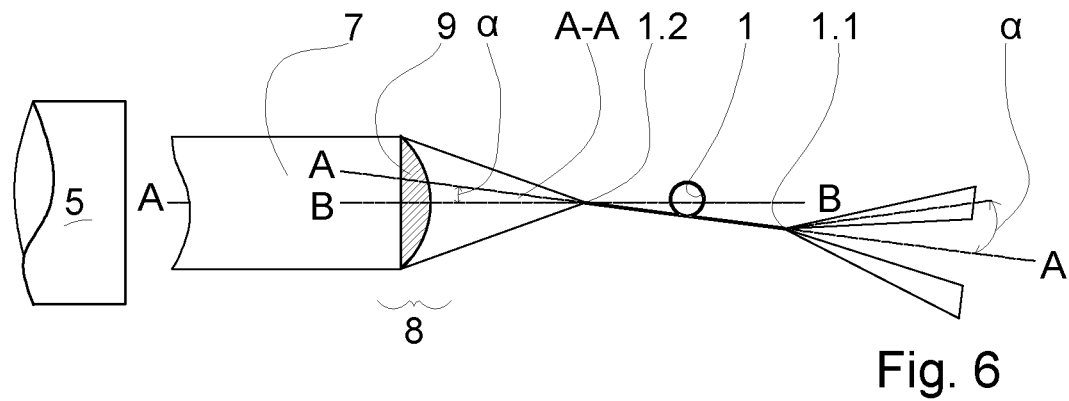
FIG. 6 is a diagram of a coupling system for coupling a laser source and an optical fiber in a further embodiment.

FIG. 6 schematically shows an embodiment of this type. Equal numbers indicate equal or equivalent parts to those described with reference to FIGS. 4 and 5. In the embodiment of FIG. 6 the optical axis of the focusing lens 9, indicated with B-B, is inclined with respect to the optical axis A-A of the optical fiber 1. The inclination is equal to an angle α. Consequently, the light radiation is injected into the optical fiber with such an inclination as to eliminate the fundamental transmission mode and, as in the previous cases, the propagation takes place by successive reflections on the interface between the core and the coating of the optical fiber, according to higher-order transmission modes. As in the previous cases, the exiting optical energy is distributed according to an internally hollow cone 3.

While in the embodiments of FIGS. 4 to 6 a large laser source 5 is used, in other embodiments the laser source can be a small semi-conductor laser source, or a plurality of semi-conductor laser sources, for example LED sources.

FIG. 7 shows a basic configuration, with a semi-conductor laser source 5 and a coupling system 8 for injecting the optical radiation into the fiber 1. The reference number 9 indicates a focusing lens. The optical axis of the lens 9 is inclined by an angle α with respect to the optical axis A-A of the optical fiber 1 at the entrance end 1.2 thereof. At the output end there is again a substantially hollow emission cone 3, with an opening angle 2α.

The use of small, i.e. compact semi-conductor laser sources allows to use a plurality of laser sources 5 arranged according to suitable configurations. FIG. 8 shows the same configuration of FIG. 7, but with a plurality of laser sources 5, in this case two laser sources arranged with the same injection angle with respect to the optical axis A-A at the entrance of the optical fiber 1. Equal numbers indicate parts and components equal to or equivalent to those of FIG. 7, which are not described again. In essence, the configuration of FIG. 7 is duplicated with a suitable inclination of the optical axes of the laser sources and of the corresponding lenses forming part of the coupling system for coupling to the optical fiber 1.

While in FIG. 8 only two laser sources 9 are shown, arranged symmetrically with respect to the optical axis A-A of the optical fiber 1, more laser sources can be provided according to the same criterion, arranged according to matrix configurations of various kinds.

For example, FIG. 8A is a schematic front view (i.e. according to the optical axis at the entrance of the fiber 1) of an arrangement of four laser sources 5 according to a matrix or linear array. The laser sources are indicated with 5A and 5B. The central position of the entrance end of the optical fiber 1 is shown in broken line. The laser sources 5A are farer from the optical axis at the entrance of the optical fiber 1, and have therefore a larger inclination with respect to this axis. The laser sources 5 B are arranged closer to the optical axis of the entrance end of the optical fiber 1 and have therefore a smaller inclination. Consequently, the exit cone 3 can have a different opening depending on which pair of laser sources 5A, 5B is turned on. If both the sources are turned on, the exit cone 3 is thicker and the optical radiation propagates according to a greater number of modes of a higher order than the fundamental mode which, as in the previously described embodiments, is eliminated as there is not a source aligned with the axis A-A of the entrance side of the optical fiber 1.

The laser sources 9 can also be arranged according to different configurations. For example, in FIG. 8B two series of laser sources 5A, 5B are provided arranged on two circular lines C1, C2, while in FIG. 8C the laser sources 5A, 5B are arranged in cross-like fashion.

Multiple laser sources may be arranged at will, provided that the inclination of the respective light beam entering the optical fiber is consistent with one of the congruence angles defined above.

In all the embodiments with multiple laser sources (FIGS. 8, 8A, 8B, 8C) there is no source in line with the optical fiber, so as to eliminate the fundamental transmission mode. Obviously, it is also possible to provide also a source in line with the entrance end 1.2 of the optical fiber 1, which is turned on when a fundamental optical energy transmission mode is required, and turned off when the fundamental transmission mode shall be eliminated.

With the described configurations particular advantages are obtained in the thermo-ablative treatments where, for the same power output, the intensity of the directive component transmitted according to the fundamental mode, i.e. in line with the optical fiber, drops drastically in favor of the secondary component(s). As previously mentioned and as shown in FIG. 3F, in this way it is possible to have round or nearly round thermal lesions allowing the use of the laser thermal ablation without the need for particular configurations of the optical fiber, for example with conical or nearly round tip, even in the case of cancers located in positions that are difficult to reach as shown in FIG. 1.

Transmitting power according to higher-order transmission modes with reduction or even elimination of the fundamental mode has also advantages in applications using diffusing fibers. A diffusing fiber is an optical fiber machined in a particular way or having at the output end a particular optical structure for transforming the directional component into a radial, i.e. lateral, or cylindrical emission. With the diffusing fibers, the power density or intensity is significantly lower, as it is distributed over a larger surface, so as to perform a sub-ablation treatment, i.e. a treatment that does not cause tissue ablation. Typically, optical fibers with diffuser are used in laser thermal therapy treatments.

In general, in all the diffusing structures there is a technical difficulty in providing a system that efficiently eliminates the residual power emitted directionally, i.e. parallel to the axis of the output end of the optical fiber. There are two advantages in suppressing the directional component in these applications. The first one is that the efficiency of the device, intended as the power diffused with respect to the total power transmitted by the fiber, is increased. Secondly, reducing or eliminating the directional component with an increase in the transversal component improves the treatment, preventing the tissues in front of the fiber from coagulating, which is generally due to localized overheating following the excessive frontally emitted power density.

Figure 9:
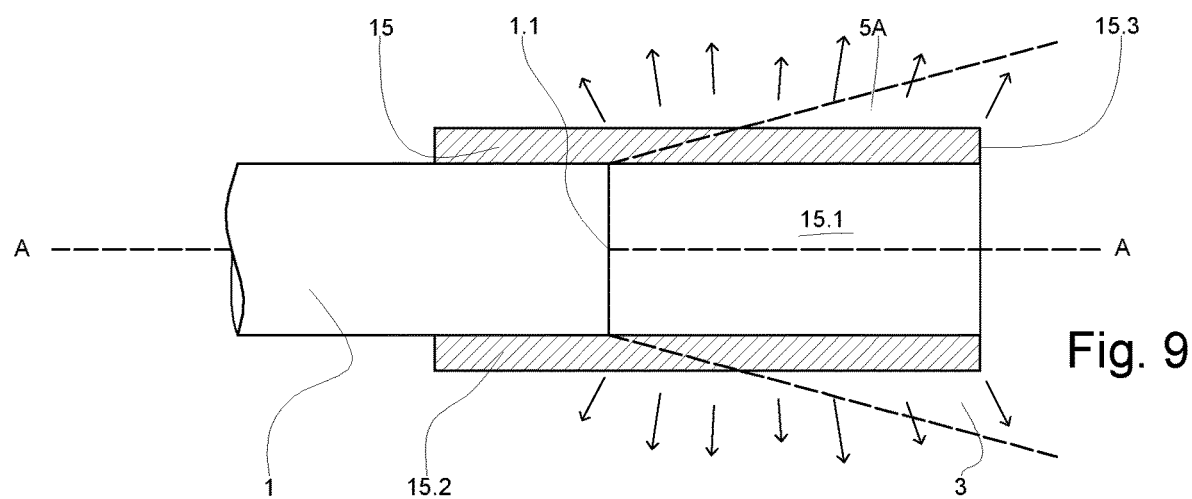
FIG. 9 is a diagram of an output end of an optical fiber with a diffuser coupled thereto.

FIG. 9 shows the output end 1.1 of an optical fiber 1, to which a diffuser 15 is applied. In the embodiment of FIG. 9 the diffuser has a hollow cylindrical shape. The output end 1.1 of the fiber 1 is inserted in the axial cavity 15.1 of the diffuser 15. Numbers 15.2 and 15.3 indicate the proximal end and the distal end of the diffuser 15, respectively. Number 3 indicates the optical radiation emission cone of the optical fiber 3. In FIG. 9 the relative position between the optical fiber 1 and the diffuser 15 is optimized, as the entire volume of the hollow emission cone 3 intersects the diffuser 15 and ends at the distal end 15.3 of the diffuser 15. In this way, the entire optical radiation conveyed by the fiber is directed into the material of the diffuser 15 and the entire volume of the diffuser 15 is exploited to diffuse the optical radiation laterally, as shown by the radial arrows in FIG. 9.

Figure 10:
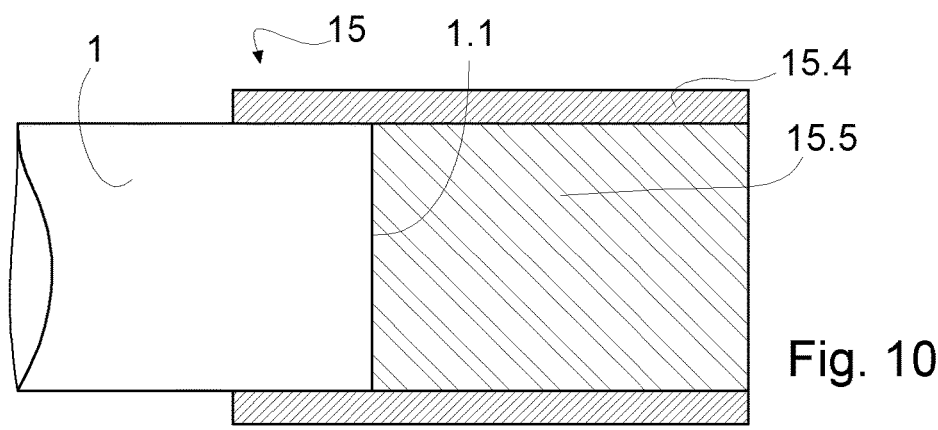
FIGS. 10, 11 and 12 show further embodiments of diffusers coupled to the output end of an optical fiber.
Figure 11:
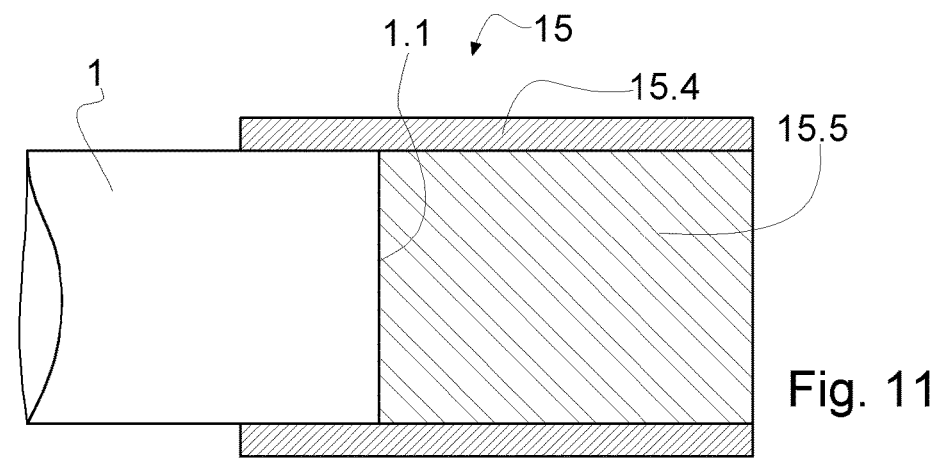
Figure 12:
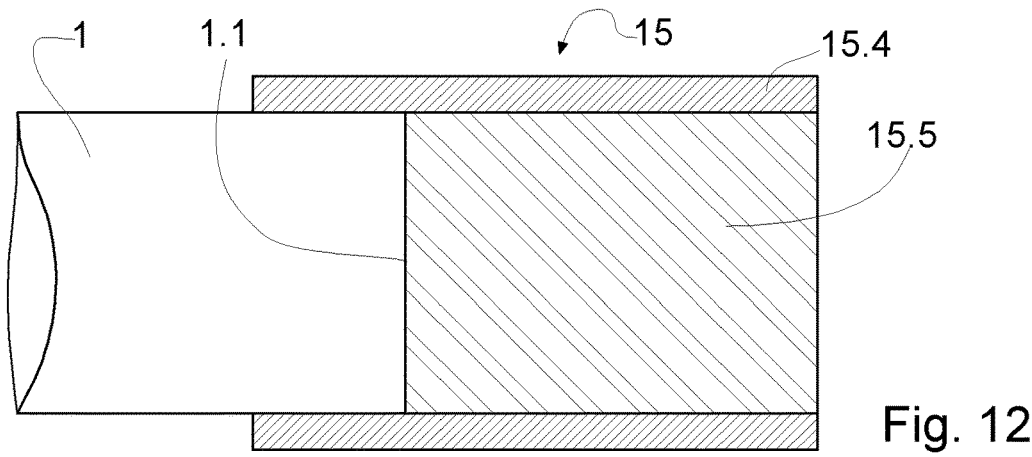

FIGS. 10, 11, and 12 show other embodiments of a diffuser 15, applied to the output end 1.1 of the optical fiber 1. In FIGS. 10, 11, and 12 the diffuser 15 is not hollow, but has an outer jacket 15.4 and an inner core 15.5. In FIG. 10 the inner core 15.5 is made of a diffusing material, whilst the outer jacket 15.4 is transparent to the wavelength of the optical radiation carried by the optical fiber 1. In FIG. 11 both the inner core 15.5 and the outer jacket 15.4 are made of a material diffusing at the wavelength of the optical radiation carried by the optical fiber 1. In FIG. 12 the inner core 15.5 is made of transparent material, whilst the outer jacket 15.4 is made of a material diffusing at the wavelength of the optical radiation carried by the optical fiber 1.

In other embodiments, the ability of the fiber to laterally emit the optical radiation is obtained through mechanical or chemical treatment of the surface of the core of the optical fiber 1 in an end portion thereof, from which the coating has been removed. The mechanical or chemical treatment of the side surface of the end portion of the core of the optical fiber 1 causes the rays incident on the treated surface to be refracted outside the fiber instead of being further refracted towards the output end 1.1 of the optical fiber 1.

Figure 13:
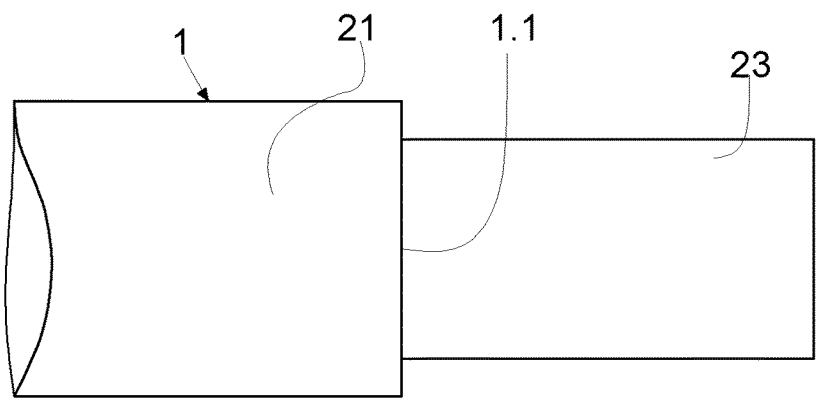
FIG. 13 shows an optical fiber with a diffuser made by working the end portion of the uncoated core.

FIG. 13 shows an embodiment of this type. The reference number 21 indicates the coating of the optical fiber 1 and number 23 indicates the core of the optical fiber 1. The coating 21 has been removed from the end portion of the optical fiber and the cylindrical surface of the core 23 has been treated to make it diffusing. The surface can be treated through different techniques, for example by means of abrasive tools, etching, laser processing, or even by introducing defects in the end portion of the core 23, or a combinations of these techniques. By eliminating the fundamental transmission mode as described herein, an improvement in the diffusion coefficient, intended as the ratio between the radially diffused component and the nominal power carried by the optical fiber 1, is also achieved.

In this embodiment, the end part of the optical fiber 1 constitutes a diffuser and the emission cone is the cone of propagation of the light radiation exiting from the part of the optical fiber 1 still coated with the coating 21, towards the part without coating 21 and treated on the surface to be made diffusing, this last part constituting a diffusing member, i.e. an optical fiber diffuser In some embodiments, the diffusing optical fiber can be housed in, or equipped with, a cooling system to keep a controlled temperature in the area of maximal emission. The cooling system allows the use of higher powers and/or a more efficient protection of the device against over-temperatures. Examples of optical fibers combined with cooling systems of this type are described in WO2018/087015; WO2018/087014; WO2018/087013; WO2018/087012.

Figure 14:
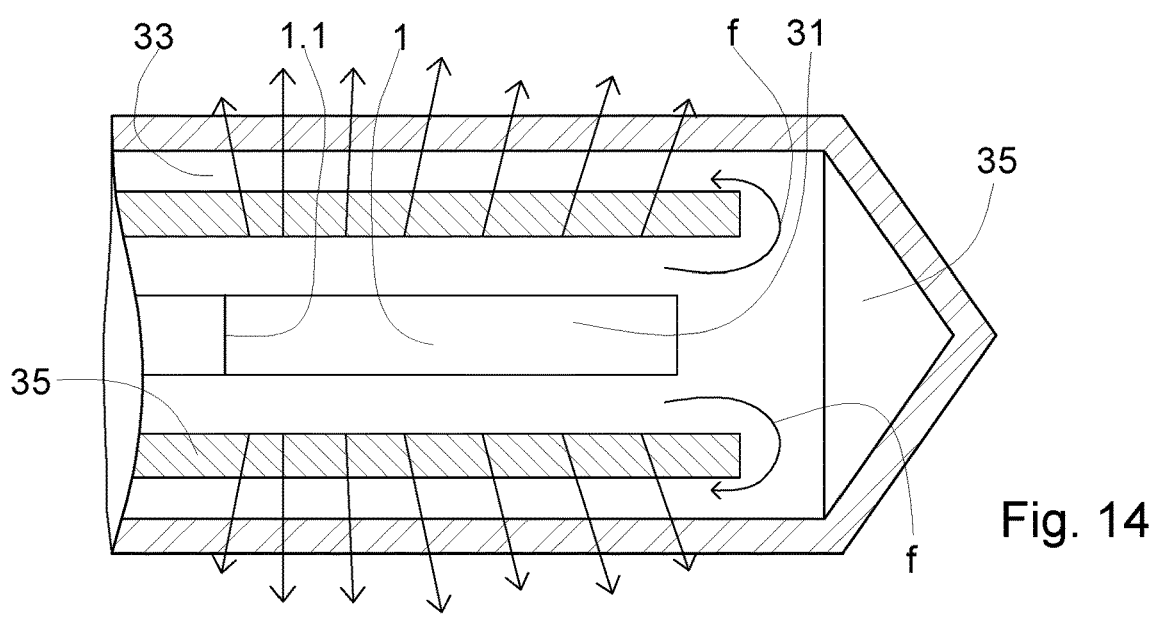
FIGS. 14, 15 and 16 show output ends of an optical fiber housed in tubular elements for a cooling fluid to circulate.

FIG. 14 schematically shows the end part of the optical fiber 1; a device is shown where the optical fiber 1 is associated with a cooling system. In FIG. 14 the optical fiber 1 with a diffuser 31 is housed inside an outer tubular element 33 and an inner tubular element 35. The diffuser 31 can be a component arranged at the output end 1.1 of the optical fiber 1, as described with reference to FIGS. 9 to 12. In other embodiments, the diffuser 31 can be constituted by the end portion of the core 23 of the optical fiber 1, worked as described with reference to FIG. 13.

The optical fiber 1 extends inside the inner tubular element 35. Between the inner tubular element 35 and the outer tubular element 33 an annular path or space for a cooling fluid is defined. The space is fluidly connected with an annular path or space formed between the optical fiber 1 and the inner tubular element 35. In this way, a cooling fluid can circulate according to the arrows f; it is fed into the gap between the optical fiber 1 and the inner tubular element 35 and is removed through the gap between the inner tubular element 35 and the outer tubular element 33. Circulation in the opposite direction is also possible, but it is less efficient. In this way, the temperature of the optical fiber 1 can be controlled by removing heat in the emission area.

The aforementioned patent publications disclose exemplary and optimized embodiments of the cooling system.

The outer tubular element 33 is closed at the front by means of a closing member 37. Having eliminated the fundamental transmission mode and, consequently, substantially reduced the power emitted frontally by the optical fiber 1 in a direction parallel to the optical exit axis, the optical energy incident onto the closing member 37 is very small or negligible. This maximizes the laterally diffused power. Furthermore, in this way it is possible to avoid or to reduce heating of the closing member 37.

The advantages described above with reference to the embodiment of FIG. 14 can be also achieved with diffusing systems, where a diffuser applied at the end of the optical fiber 1 or formed on the end portion of the core 23 of the optical fiber is not provided.

Figure 15:
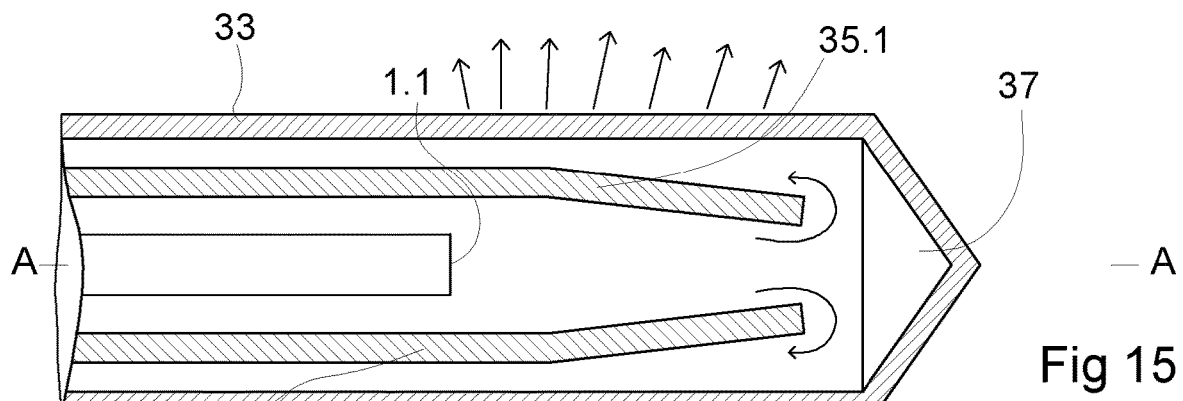

FIG. 15 illustrates, for example, an embodiment where the optical fiber 1 ends with the output end 1.1 in an inner tubular element 35, without a diffuser 31 being provided. The inner tubular element 35 is housed in an external tubular element 33, so as to define for example a cooling circuit similar to that described with reference to FIG. 14.

In the embodiment of FIG. 15, at least the end portion 35.1 of the inner tubular element 35 is diffusing at the wavelength of the optical radiation carried by the optical fiber 1. The optical beam exiting from the output end 1.1 of the optical fiber 1 diverges according to an angle $2\alpha$ (wherein $\alpha$ is the angle by which the optical radiation is injected into the optical fiber 1) and is incident onto the inner surface of the inner tubular element 35, thus being diffused outwards.

The outer tubular element 33 can be diffusing, or preferably transparent to the wavelength of the optical radiation conveyed by the optical fiber 1.

In advantageous embodiments, it is possible to provide the end portion 35.1 of the inner tubular element 35 with a conical shape, as shown in FIG. 15, to better collect the optical radiation emitted by the optical fiber 1. In this case again, the elimination or substantial reduction of the power transmitted according to the fundamental mode increases the ratio between laterally diffused power and total power conveyed in the optical fiber. The power incident onto the front closing member 37 is reduced and the energy efficiency of the device is improved.

Figure 16:
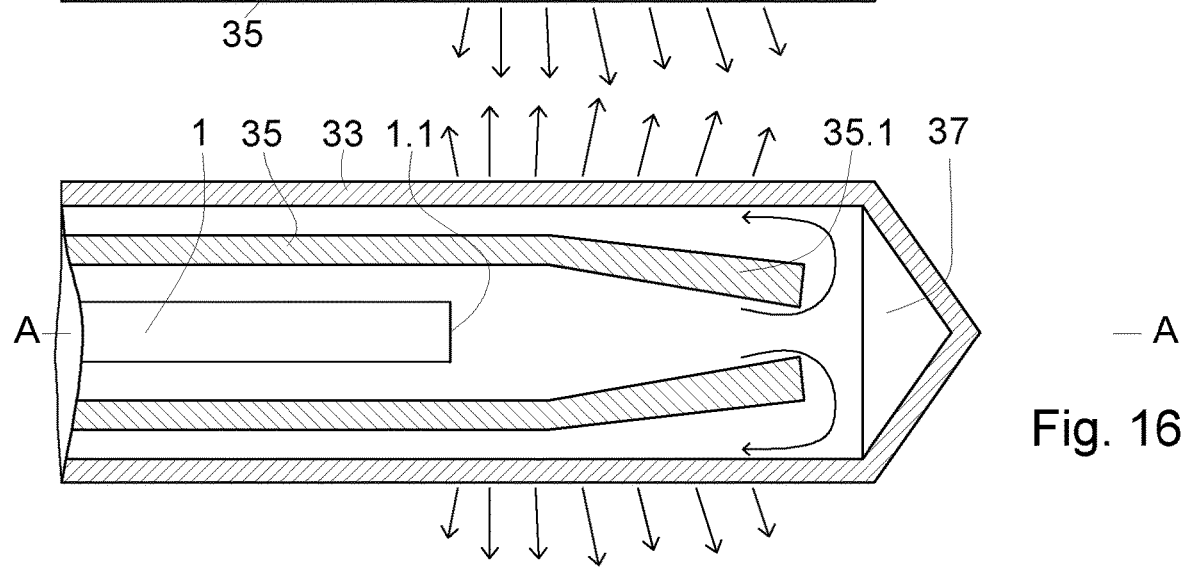

FIG. 16 shows an embodiment similar to that of FIG. 15, in which identical numbers indicate parts identical or corresponding to those of FIG. 15, not described again. The main difference between the embodiment of FIG. 15 and the embodiment of FIG. 16 is that the end portion 35.1 of the inner tubular element 35 is no longer conical, as in FIG. 15, but has an outer cylindrical surface and a variable thickness; consequently, a hollow inner volume of tapered shape, for example conical shape, is therefore formed, for better intercepting the optical emission exiting from the output end 1.1 of the optical fiber 1.

Injecting the optical radiation into the optical fiber according to an angle different than zero, in order to have a substantial suppression of the fundamental transmission mode and the consequent distribution of the exiting optical power according to a hollow cone and reduction or elimination of frontal emission, ensures many advantages also with devices for laser thermal therapy that use an inflatable balloon. Devices of this type comprise an expandable body, hereinafter referred to simply as a balloon, associated with the output end of the optical fiber. The balloon is expanded by means of a filling fluid, for example a liquid, once the end of the optical fiber with the balloon associated therewith has been brought up to the required position in the organ to be treated. The expansion of the balloon generates a cavity in the tissue in which the fiber is inserted. The laser radiation is irradiated as isotropically as possible through the balloon walls. Examples of devices of this type are described in U.S. Pat. No. 8,740,957.

Figure 17:
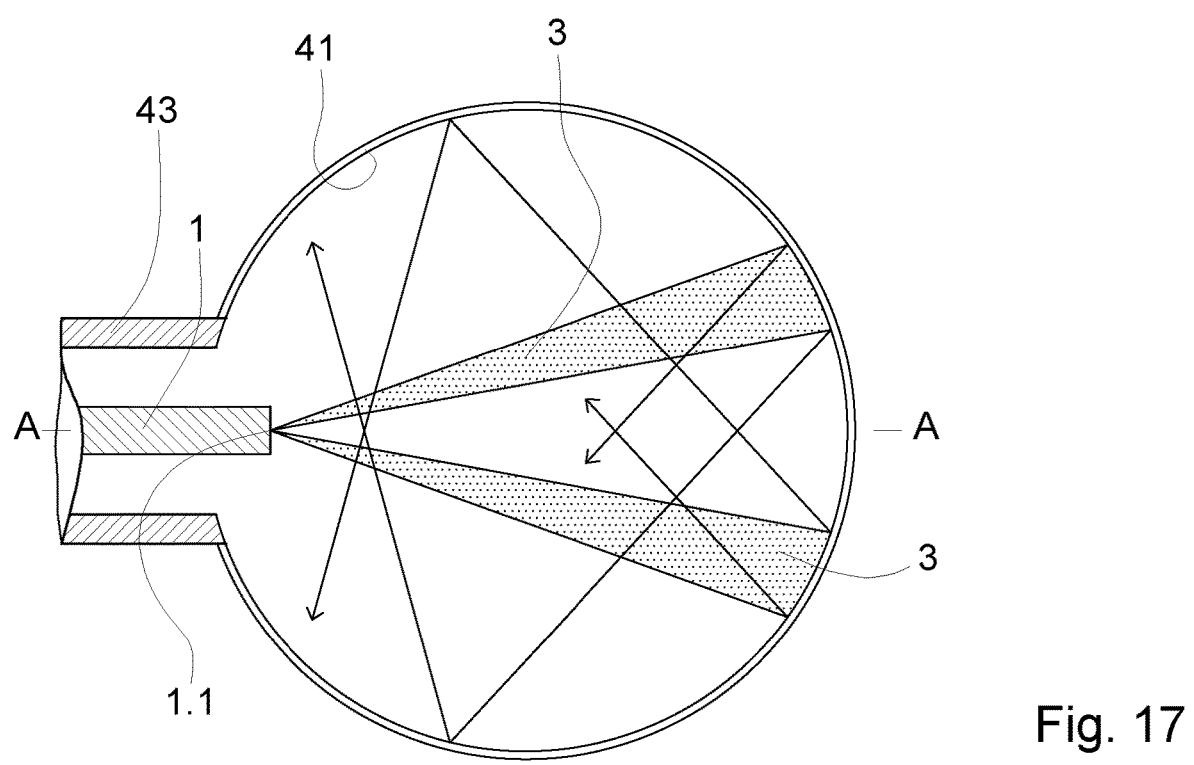
FIGS. 17 and 18 show the end of an optical fiber with an expandable balloon in two embodiments.

FIG. 17 schematically shows the distal end of an optical fiber 1, to which a balloon 41 is associated. In the embodiment of FIG. 17 the optical fiber 1 is housed in a catheter 43, at the distal end of which the balloon 41 is applied.

The optical radiation conveyed in the optical fiber 1 is emitted according to the cone 3, with elimination or substantial reduction of the frontal emission due to the elimination of the fundamental transmission mode of the optical radiation in the optical fiber. The directional longitudinal emission is therefore drastically reduced or suppressed. The radiation according to the cone 3 is incident onto the wall of the balloon 41. At the point of incidence of the ray onto the inner surface of the balloon 41 a refracted component is generated, which exits from the wall of the balloon 41 and penetrates the surrounding tissue, and a reflected component, which remains trapped in the balloon and hits again the surface of the balloon and will be subdivided again into a refracted component and a reflected component. Then, each entering ray gradually transfers its energy to the surrounding tissues due to the subdivision into reflected component and refracted component at each impact with the balloon surface 41.

In this way the tissue in contact with the balloon 41 is irradiated with an intensity which is reduced according to the ratio between the balloon surface and the emitting surface of the fiber. This is advantageous because it is possible to have a total energy approximately equivalent to that of the bare, i.e. uncooled, fiber without bringing the tissue in contact with the fiber up to at high temperatures. An excessive heating could lead to the creation of a cavity around the fiber, for the most part of the tissue evaporation and sublimation treatment. In case they are not necessary for the treatment, tissue evaporation and/or sublimation represent a waste of part of the energy which is involved in tissue phase change. Vice versa, by using the balloon 41, the energy is used for denaturating tissues, starting from that in contact with the balloon and continuing with the tissue following along the transmission path, with a gradual reduction of the radiation intensity. The radiation propagates in the tissue until its intensity is below the critical threshold where tissue can be irreversibly damaged and up to the complete safe absorption of energy in the following tissues.

Therefore, the balloon 41 acts as an integrating sphere and makes the emission of optical power in the surrounding tissue uniform, i.e. substantially isotropic. Also the fluid fed into the balloon to inflate it can be diffusing. For example, the fluid may contain diffusing particles in suspension or in emulsion, which make the emission isotropic. Injecting the optical radiation from the optical fiber 1 into the balloon 41 according to a cone 3, reducing or eliminating the directional component of the fundamental transmission mode, substantially contributes to the efficiency of the system and to the emission isotropy.

Figure 18:
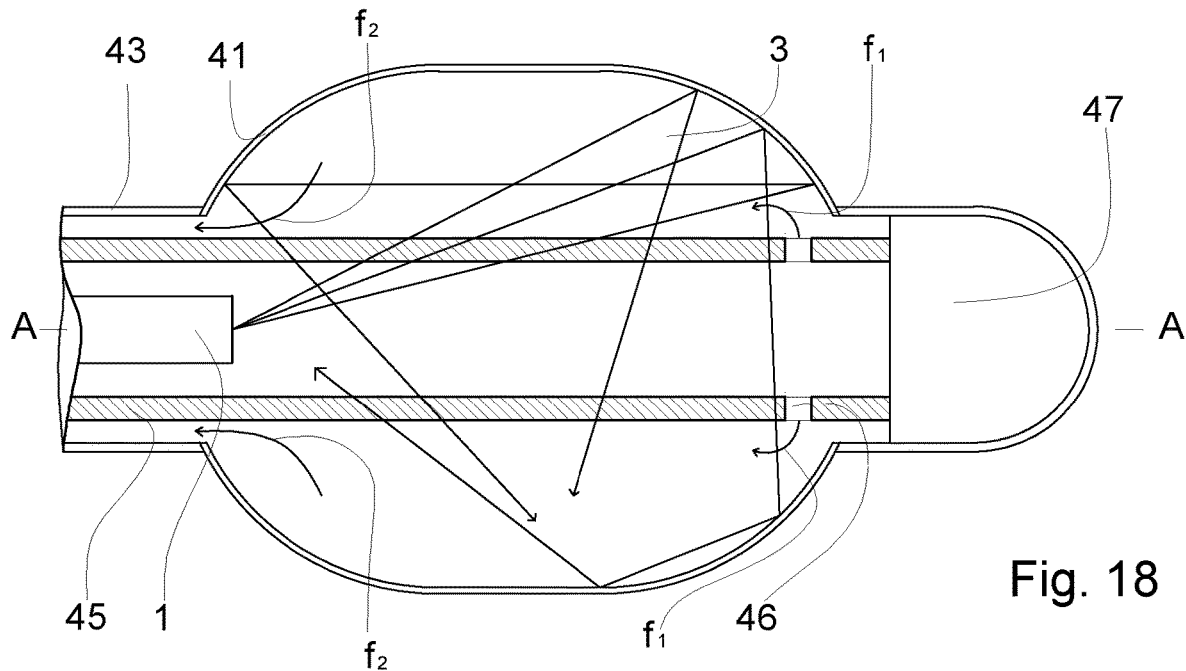

FIG. 18 shows a balloon device according to a further embodiment. The same numbers indicate identical or equivalent parts to those in FIG. 17. In the embodiment of FIG. 18 the optical fiber 1 is housed in a system comprised of two substantially coaxial tubular elements arranged inside each other. In more detail, the system comprises an outer tubular element 43, consisting of an introduction needle or catheter for example, and an inner tubular element 45, arranged inside each other. The optical fiber 1 is housed in the inner tubular element 45.

The inner tubular element 45 can be transparent to the wavelength of the optical radiation conveyed by the optical fiber 1. In some embodiments, the inner tubular element 45 comprises one or more openings 46 connecting the inside of the inner tubular element 45, where the optical fiber 1 is housed, and the inside of the outer tubular element 43.

In this way a circuit is defined, where a fluid can circulate according to arrows f1, f2. In FIG. 18 the fluid circulates from the inside towards the outside, for better cooling the optical fiber 1, but it can also circulate in opposite direction. The circulating fluid also expands the balloon 41.

FIG. 18 shows, for simplicity and clarity of representation, only half of the emission cone 3 of the radiation transmitted along the optical fiber 1 and exiting from the output end 1.1. As in FIG. 17, in the configuration of FIG. 18 again the radiation is reflected and refracted several times on the surface of the balloon 41, with a consequent substantially isotropic radiation emission. A closing element 47 is applied to the terminal end of the inner tubular element 45. The distal end of the inner tubular element 45 and the distal end of the outer tubular element 43 are fixed to the closing element. Eliminating or substantially reducing the directional emission, parallel to the axis A-A of the optical fiber 1, reduces or eliminates the power incident on the closing element 47, with a consequent increase in the energy efficiency of the system and preventing problems due to localized overheating of the closing element 47.

The optical fibers used for laser thermal ablation or thermal therapy are usually fibers for disposable use or fibers that can be sterilized and used repeatedly. For saving costs in case of fibers for disposable use, as well as for simplifying the sterilization cycles in case of fibers for multiple use, it is therefore advisable that the light guide from the laser source to the output end is subdivided into a portion not to be replaced or sterilized, and a replaceable outer portion.

Figure 19:
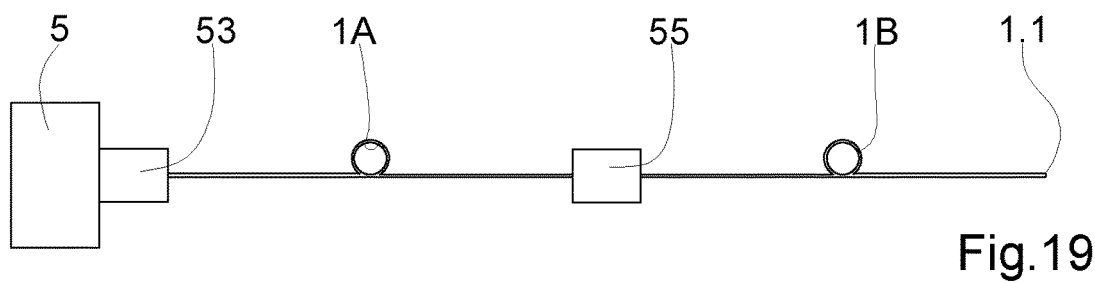
FIG. 19 shows a system with a laser source, an injection device and a system made of two fibers joined by means of an optical coupler.

FIG. 19 shows a diagram of a laser treatment apparatus comprising a laser source 5, a first optical fiber 1A and a second optical fiber 1B. The optical fiber 1B has an output end 1.1 designed to be introduced into the patient's body. The optical fiber 1A is connected, at the proximal end thereof, to the laser source 5 through a connector 53, and is connected, at the distal end thereof, to the optical fiber 1B through an optical coupler 55. In this kind of system, there are two points where the radiation can be injected into the fiber according to such an angle as to eliminate the fundamental transmission mode and facilitate higher-order transmission modes. These two points are in at the connector 53 and at the optical coupler 55.

Figure 20:
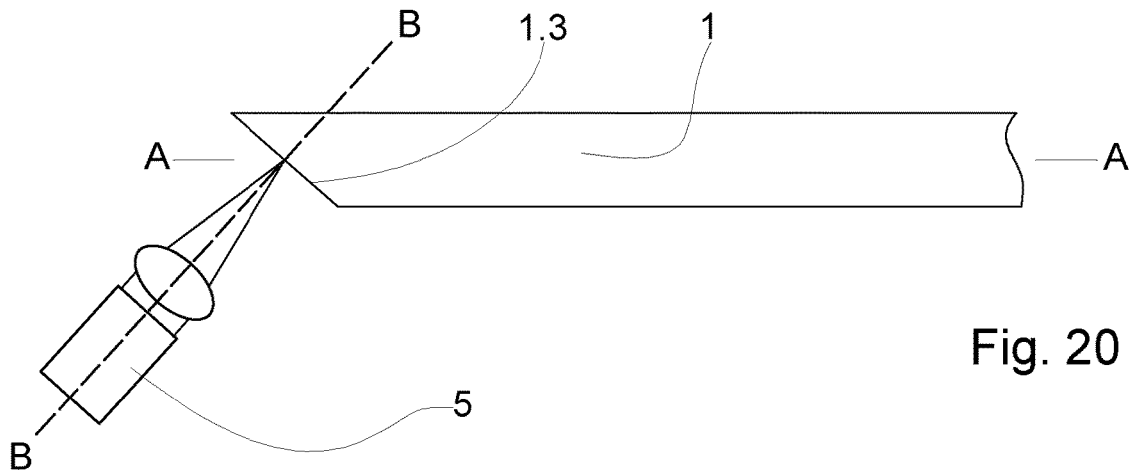
FIG. 20 shows a coupling system for coupling a laser source and optical fiber, wherein the entrance end of the optical fiber is so configured as to increase the coupling efficiency.
Figure 21:
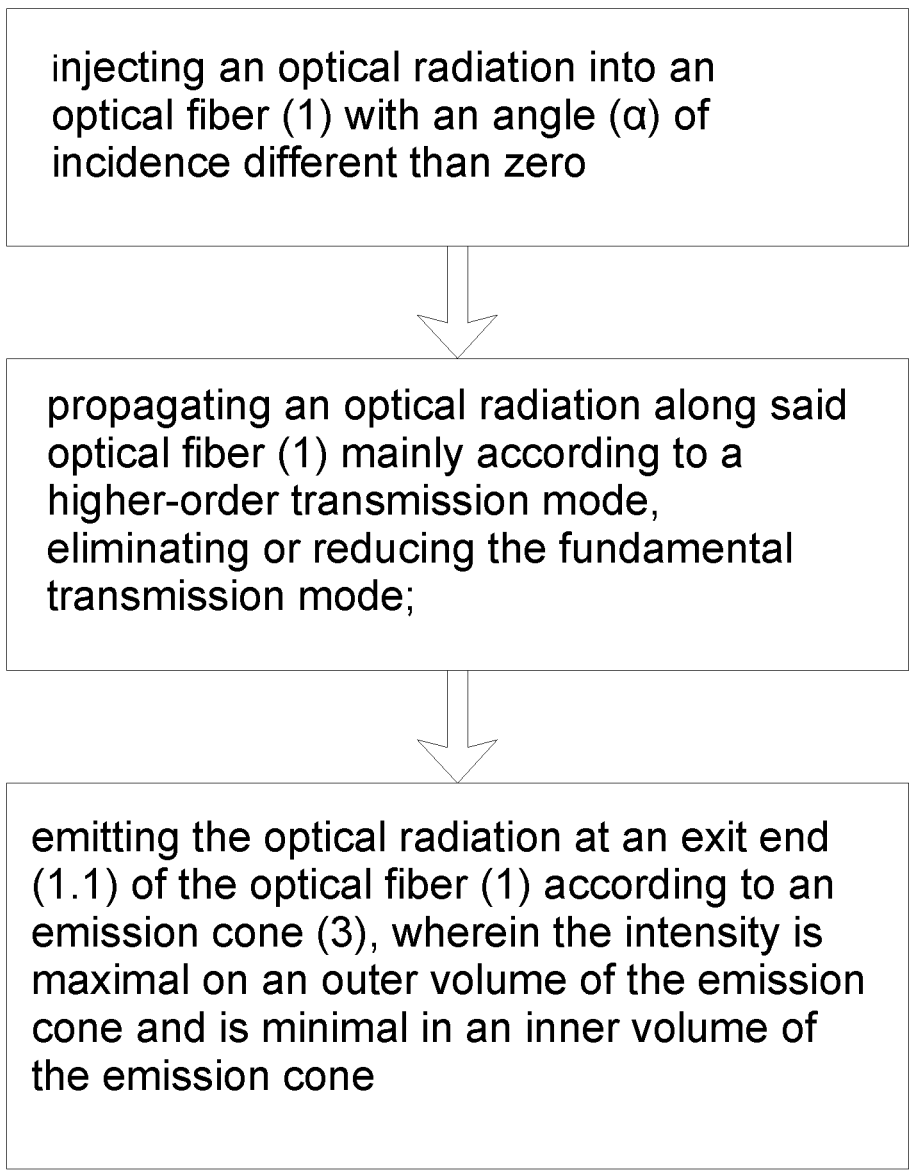
FIGS. 21, 22, 23, 24 and 25 show flowcharts summarizing the methods that can be carried out with the device described herein.
Figure 22:
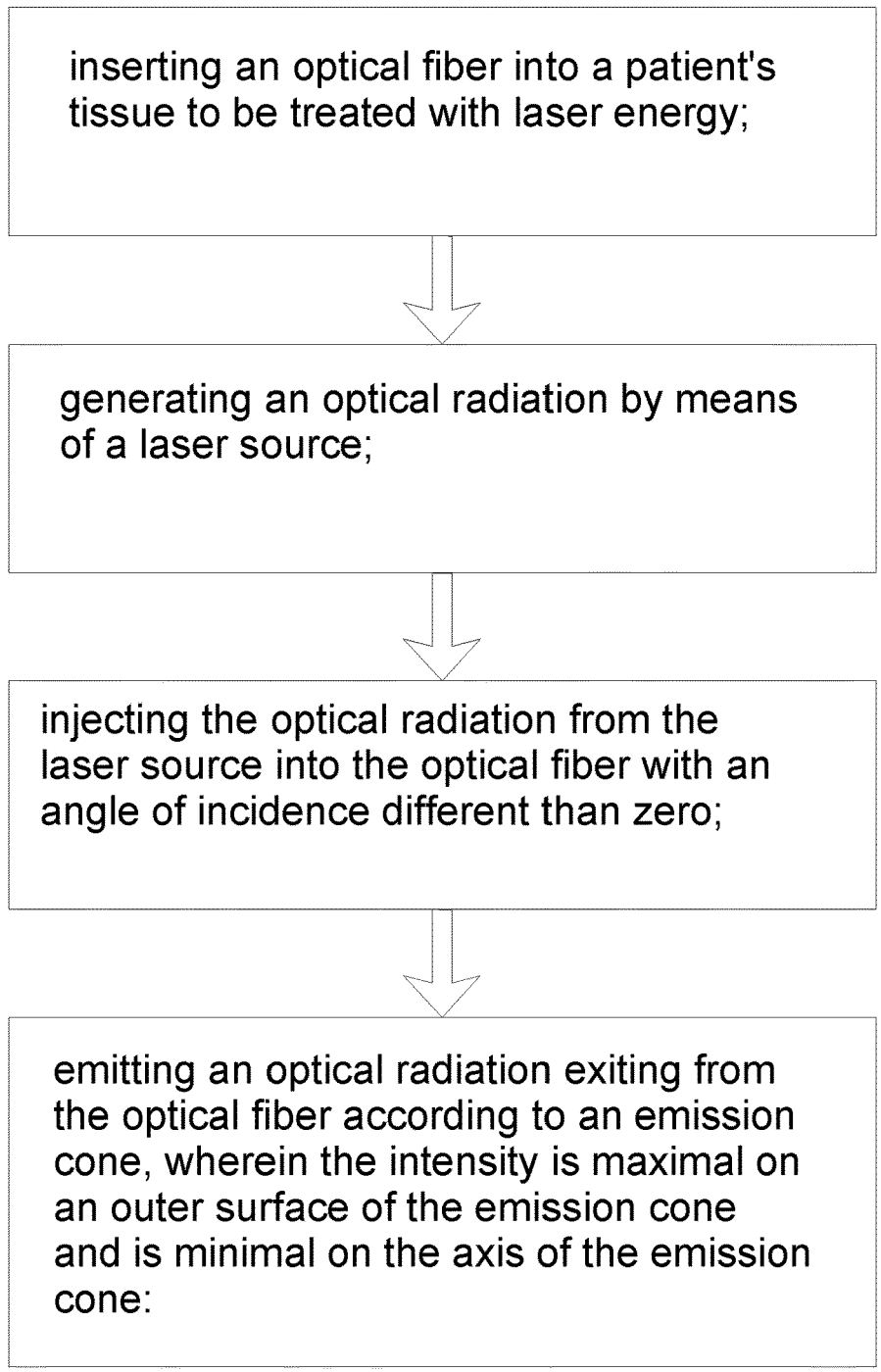
Figure 23:
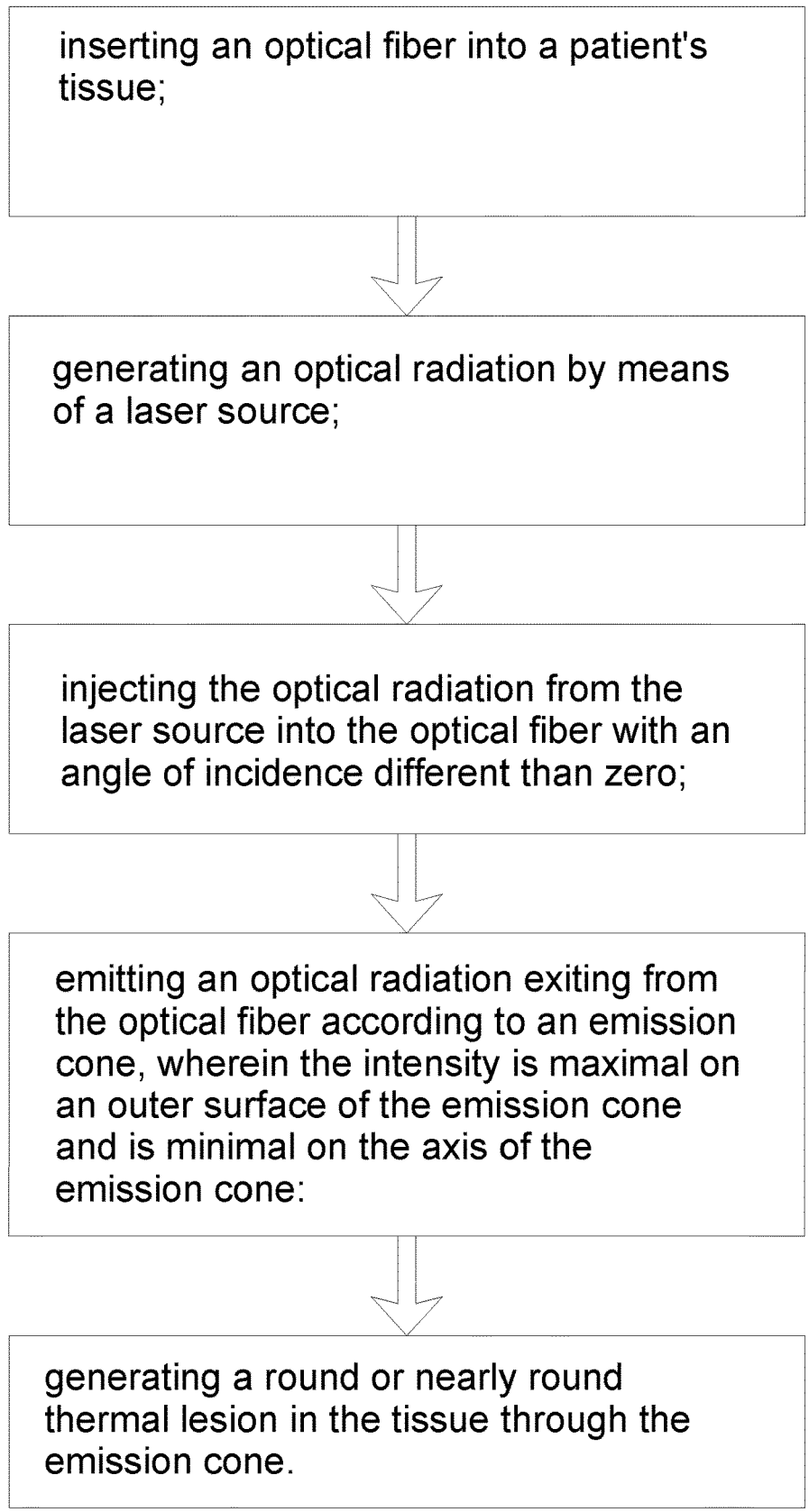
Figure 24:
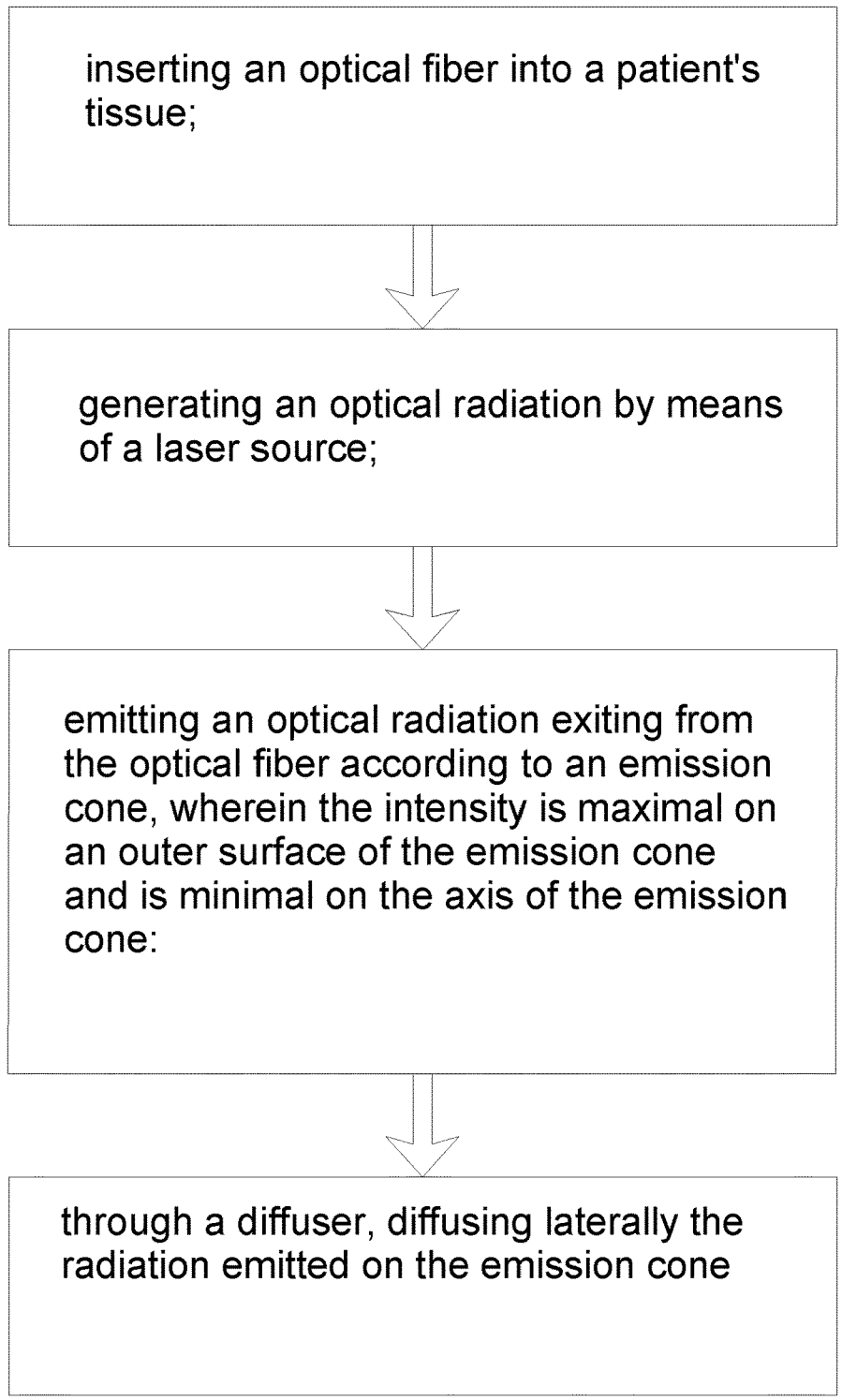
Figure 25:
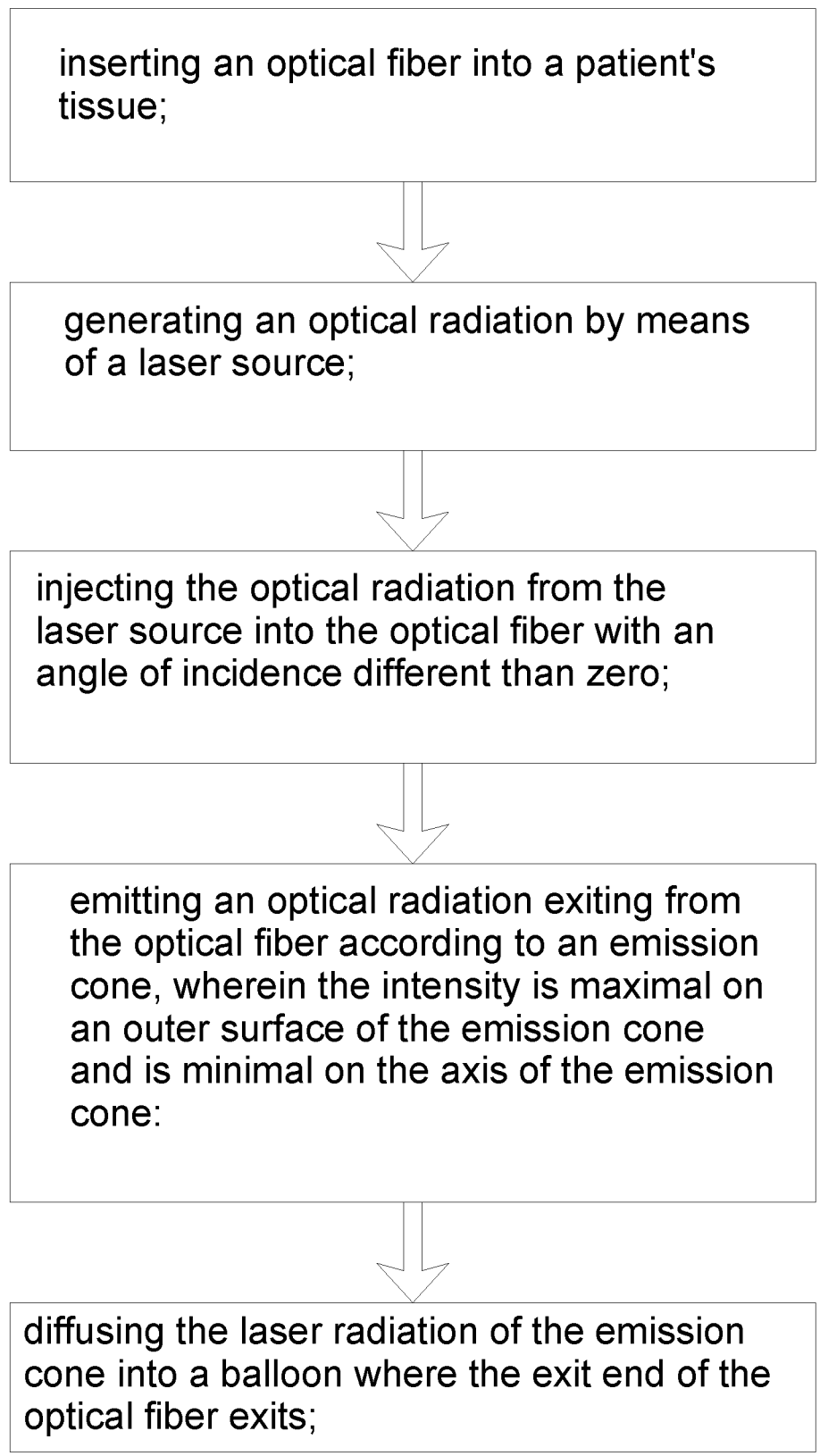

According to some embodiments, the efficiency of injecting the optical radiation into the optical fiber 1 obliquely can be increased by using a particular embodiment of the entrance end 1.2 of the optical fiber 1. A suitable embodiment to increase the efficiency of the device is illustrated in FIG. 20, where entrance end 1.2 of an optical fiber 1 and a laser source 5 are shown. The axis of the optical fiber is indicated with A-A, whilst B-B indicates the optical axis of the laser source 5. As shown in FIG. 20, the entrance surface 1.3 of the optical fiber 1 is treated so as to be inclined by an angle equal to (90°-α), i.e. a complementary angle of the angle α, which is the angle between the axis B-B and the axis A-A. In this case, the laser beam is orthogonal to the entrance surface 1.3; this allows to minimize the reflection coefficient and therefore the amount of radiation entering the optical fiber 1 to be guided towards the output end 1.1.

Figure 26:
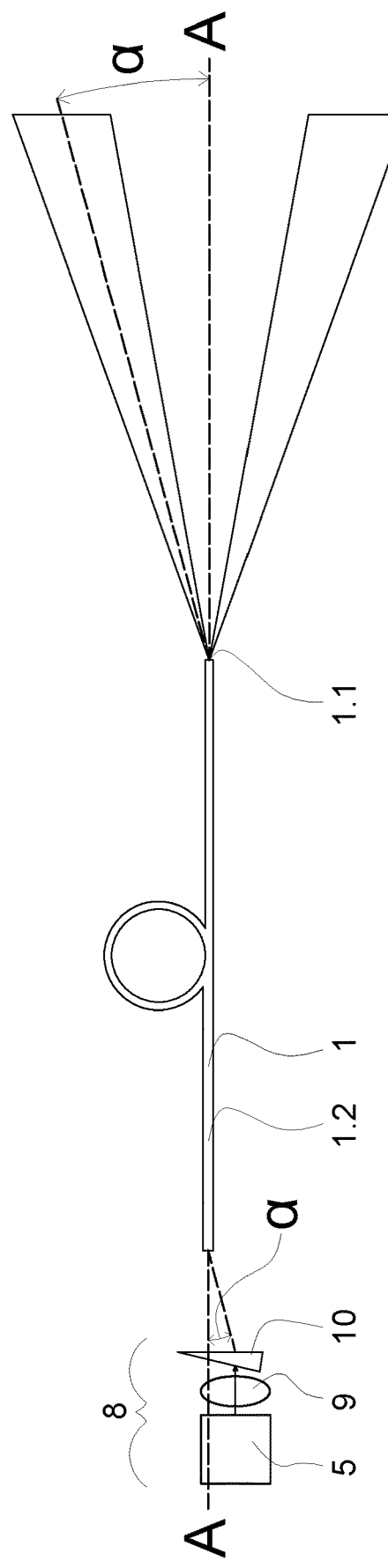
FIG. 26 is a diagram of a coupling system for coupling a laser source and an optical fiber in a further embodiment.

FIG. 26 schematically shows a further embodiment of a system for obliquely injecting optical radiation into an optical fiber. Number 5 indicates a laser source, for example a semi-conductor laser source, and number 8 indicates a generic coupling system for injecting the optical radiation into the fiber 1. The reference number 9 indicates a focusing lens. The optical axis of the lens 9 is parallel to the optical axis A-A of the optical fiber 1. A prism 10 is arranged between the focusing lens 9 and the entrance 1.2 of the optical fiber 1. The axis of the laser beam, which propagates parallel to the axis A-A of the optical fiber 1 up to the prism 10, is deviated by this latter so as to enter the optical fiber 1 inclined by an angle α with respect to the A-A axis of the fiber. In this case again, at the output end there is a substantially hollow emission cone 3, with an opening angle 2α.

According to a further development of the systems and devices described herein, the opening of the exiting beam can be further increased in order to have a better distribution of energy, using particular configurations of the optical fiber 1. The following description can be applied in combination with any of the embodiments described above, independently of the structure of the laser source(s) used and of the laser-fiber coupling system.

Figure 27:
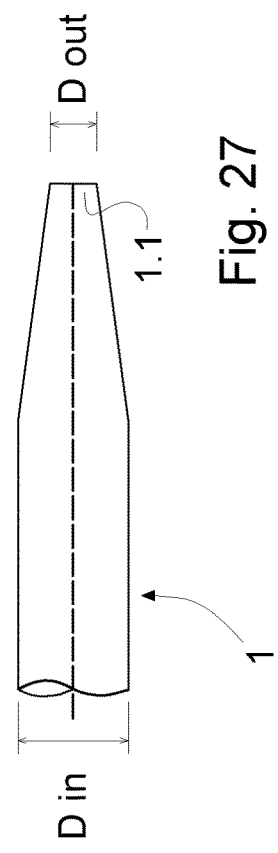
FIG. 27 is a diagram of an end portion of a tapered fiber.

In the embodiments described herein the optical fiber 1 can be tapered and have an entrance diameter Din larger than the output diameter Dout. For example, the optical fiber 1 can have a tapered end portion in the exit area. FIG. 27 schematically shows the end part of a tapered optical fiber 1, and number 1.1 indicates the output end again. It has been found that by using a tapered fiber of this type with any of the coupling systems described above, through which a conical exiting beam is obtained, the opening of the exiting beam is wider than it would be with a non-tapered fiber, given the same coupling system.

Figure 28A:
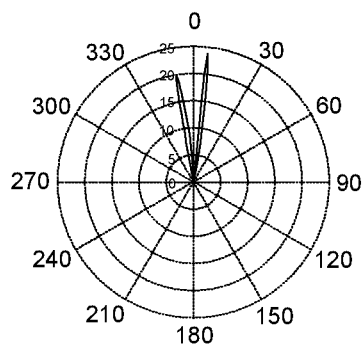
FIGS. 28A, 28B, 28C, 28D are polar comparison charts illustrating the effectiveness of using tapered fibers in combination with system for injecting inclined laser beams into optical fibers.
Figure 28B:
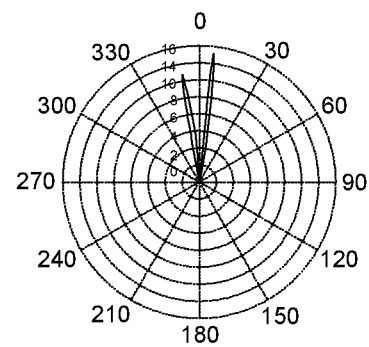
Figure 28C:
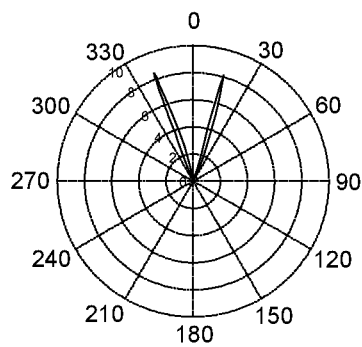
Figure 28D:
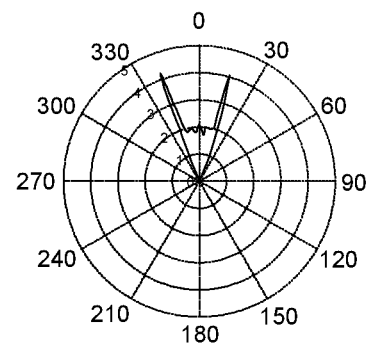

FIGS. 28A, 28B, 28C, 28D are polar emission charts, similar to those of FIGS. 2A, 2C, 3A, 3C, illustrating the effectiveness of using a tapered fiber in combination with a system for injecting inclined laser beams into optical fibers. More particularly, FIG. 28A shows the radiation chart obtained with a normal, non-tapered fiber, the diameter whereof is 272 μm. The exit angle is 14°. FIG. 28B shows the radiation chart with the same coupling system of FIG. 28A but with a slightly tapered optical fiber 1, whose entrance diameter is 272 μm and exit diameter is 200 μm. The exit angle of the laser beam was found to be 21°. FIGS. 28C and 28D show charts with the same coupling system and a fiber whose entrance diameter is 272 μm and exit diameters are 150 μm and 100 μm, respectively. The angle of the exiting beam is 33° and 40°, respectively, significantly improving the beam spreading effect given the same entrance angle. The greater the tapering of the optical fiber between entrance and exit, the greater the widening of the exiting beam.

With this kind of device it is possible to perform laser thermal ablation treatments, laser thermal therapy treatments, or other laser treatments on organs or tissues in vivo, for various applications. Basically, a treatment method with the described device can comprise the following steps:

inserting an optical fiber into a tissue of a patient requiring a treatment;
generating an optical radiation through a laser source;
injecting the optical radiation of the laser source into the optical fiber with an injection angle with respect to an optical axis of the optical fiber, different than zero and smaller than an acceptance angle of the optical fiber;
emitting an optical radiation at an output end of the optical fiber according to an emission cone, wherein the intensity of the exiting optical radiation is maximal on an outer surface of the emission cone and is minimal on the axis of the emission cone.

In case the patient requires a laser thermal ablation treatment, the method may further comprise the step of generating a round or nearly round thermal lesion in the tissue through the emission cone. A nearly round lesion means a lesion wherein the sphericity ration is greater than 0.7, preferably equal to or greater than 0.8, for example equal to or greater than 0.85 or 0.9.

For laser thermal therapy, the method may further comprise the step of laterally diffusing, through a diffuser and/or through treatment of the output end of the optical fiber, the radiation emitted on the emission cone.

In other embodiments, the method may comprise the step of diffusing the laser radiation of the emission cone into a balloon where the optical fiber exits; and the step of diffusing the radiation, through the balloon, into the surrounding tissue, where the balloon has been inserted and inflated.

FIGS. 21 to 25 illustrate flow charts summarizing the methods described above.

The invention claimed is:

1. A device comprising:
   at least a laser source;
   an optical fiber with an optical radiation entrance end and an optical radiation output end;
   a coupling system for coupling the laser source and the optical fiber, adapted to inject an optical radiation emitted by the laser source into the entrance end of the optical fiber; wherein: the optical fiber is a multi-mode optical fiber; the coupling system is adapted to inject the optical radiation into the optical fiber with such an inclination as to reduce or eliminate a fundamental transmission mode and to promote transmission according to at least one higher-order transmission mode, so that the optical radiation at the output end of the optical fiber has a cone-shaped distribution wherein the intensity is maximal in a peripheral volume of an emission cone and is minimal inside the emission cone, wherein the coupling system comprises a focusing lens for focusing the optical radiation at the entrance end of the optical fiber, and wherein the focusing lens comprises a central portion where the optical radiation received by the lens is not focused on the entrance end of the optical fiber.

2. The device of claim 1, wherein the optical fiber is tapered towards the output end.

3. The device of claim 1, wherein the maximal intensity of the optical radiation at the output end of the optical fiber in the peripheral volume of the emission cone is at least twice the minimal intensity in a central volume of the emission cone.

4. The device of claim 1, wherein the coupling system is adapted to inject into the optical fiber an optical radiation beam having an inclination different than zero with respect to an axis of the optical fiber, said inclination being smaller than an acceptance angle of the optical fiber.

5. The device of claim 1, wherein the output end of the optical fiber is substantially flat.

6. The device of claim 1, wherein the coupling system is such that the optical radiation exiting from the optical fiber has an opening cone of at least 10°.

7. The device of claim 1, wherein the focusing lens comprises a hole or a central shield, in correspondence of which the optical radiation incident on the focusing lens is not focused to the entrance end of the optical fiber.

8. The device of claim 1, further comprising a diffuser arranged at the output end of the optical fiber.

9. The device of claim 1, wherein a side surface of a distal portion of the core of the optical fiber, adjacent to the output end, has a surface treatment adapted to facilitate the lateral diffusion of the optical radiation.

10. The device of claim 1, comprising an outer tubular element and an inner tubular element, inserted inside each other; wherein the optical fiber extends inside the inner tubular element; and wherein the outer tubular element and the inner tubular element define a path for circulation of a cooling fluid.

11. The device of claim 10, wherein the inner tubular element is diffusing at the wavelength of the optical radiation emitted by the optical fiber, and wherein the outer tubular element is diffusing or transparent at the wavelength of the optical radiation emitted by the optical fiber.

12. The device of claim 1, further comprising a tubular element, wherein the optical fiber is housed inside the tubular element, which is provided, near the output end of the optical fiber, with an expandable member.

13. An electro-medical apparatus comprising the device of claim 1.

14. A device comprising:
   at least a laser source;
   an optical fiber with an optical radiation entrance end and an optical radiation output end;
   a coupling system for coupling the laser source and the optical fiber, adapted to inject an optical radiation emitted by the laser source into the entrance end of the optical fiber; wherein: the optical fiber is a multi-mode optical fiber; the coupling system is adapted to inject the optical radiation into the optical fiber with such an inclination as to reduce or eliminate a fundamental transmission mode and to promote transmission according to at least one higher-order transmission mode, so that the optical radiation at the output end of the optical fiber has a cone-shaped distribution wherein the intensity is maximal in a peripheral volume of an emission cone and is minimal inside the emission cone, wherein the coupling system comprises a focusing lens having an optical axis that is inclined, with respect to the optical axis of the optical fiber, by an angle greater than zero and smaller than the acceptance angle of the optical fiber.

15. The device of claim 14, wherein the optical fiber is tapered towards the output end.

16. The device of claim 14, wherein the maximal intensity of the optical radiation at the output end of the optical fiber in the peripheral volume of the emission cone is at least twice the minimal intensity in a central volume of the emission cone.

17. The device of claim 14, wherein the coupling system is adapted to inject into the optical fiber an optical radiation beam having an inclination different than zero with respect to an axis of the optical fiber, said inclination being smaller than an acceptance angle of the optical fiber.

18. The device of claim 14, wherein the output end of the optical fiber is substantially flat.

19. The device of claim 14, wherein the coupling system is such that the optical radiation exiting from the optical fiber has an opening cone of at least 10°.

20. The device of claim 14, further comprising a diffuser arranged at the output end of the optical fiber.

21. The device of claim 14, wherein a side surface of a distal portion of the core of the optical fiber, adjacent to the output end, has a surface treatment adapted to facilitate the lateral diffusion of the optical radiation.

22. The device of claim 14, further comprising an outer tubular element and an inner tubular element, inserted inside each other; wherein the optical fiber extends inside the inner tubular element; and wherein the outer tubular element and the inner tubular element define a path for circulation of a cooling fluid.

23. The device of claim 22, wherein the inner tubular element is diffusing at the wavelength of the optical radiation emitted by the optical fiber, and wherein the outer tubular element is diffusing or transparent at the wavelength of the optical radiation emitted by the optical fiber.

24. The device of claim 14, further comprising a tubular element, wherein the optical fiber is housed inside the tubular element, which is provided, near the output end of the optical fiber, with an expandable member.

25. An electro-medical apparatus comprising the device of claim 14.

* * * * *